US012588871B2

(12) United States Patent
Jung et al.

(10) Patent No.: US 12,588,871 B2
(45) Date of Patent: Mar. 31, 2026

(54) METHOD FOR CALIBRATING EXTERNAL LIGHT FOR BIO-SIGNAL MEASUREMENT, AND ELECTRONIC DEVICE AND STORAGE MEDIUM THEREFOR

(71) Applicant: Samsung Electronics Co., Ltd., Gyeonggi-do (KR)

(72) Inventors: Hyunjun Jung, Gyeonggi-do (KR); Daehyeong Lim, Gyeonggi-do (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 546 days.

(21) Appl. No.: 18/087,904

(22) Filed: Dec. 23, 2022

(65) Prior Publication Data

US 2023/0135923 A1     May 4, 2023

Related U.S. Application Data

(63) Continuation of application No. PCT/KR2021/004704, filed on Apr. 14, 2021.

(30) Foreign Application Priority Data

Jun. 26, 2020     (KR) ........................ 10-2020-0078155

(51) Int. Cl.
*A61B 5/00*          (2006.01)
(52) U.S. Cl.
CPC ............ *A61B 5/681* (2013.01); *A61B 5/7225* (2013.01); *A61B 2560/0238* (2013.01)
(58) Field of Classification Search
CPC ................ A61B 2560/0247; A61B 2560/0238
See application file for complete search history.

(56) References Cited

U.S. PATENT DOCUMENTS 5,954,644 A * 9/1999 Dettling ............. A61B 5/14552
                                                          600/336
10,426,387 B2 10/2019 Barrett
(Continued)

FOREIGN PATENT DOCUMENTS

CN          106473728 A      3/2017
JP          9-299342 A       11/1997
(Continued)

OTHER PUBLICATIONS

International Search Report dated Jul. 22, 2021.
(Continued)

*Primary Examiner* — Uzma Alam
*Assistant Examiner* — Alexandria Mendoza
(74) *Attorney, Agent, or Firm* — Sughrue Mion, PLLC

(57)          ABSTRACT

According to certain embodiments, a wearable electronic device, comprises: at least one light receiving unit; at least one light emitting unit; an external light calibration circuit; and a processor electrically connected with the at least one light receiving unit, at least one light emitting unit, and the external light calibration circuit, wherein the processor is configured to: control the at least one light emitting unit to radiate light during first periods, and not emit light during second periods, and detect light through the at least one light receiving unit during the second periods, and controlling the external light calibration circuit to provide an input to the at least one light receiving unit during first periods, based on the light detected during the second periods; and wherein during the first periods the at least one light receiving unit provides an output based on light received, and the input from the external light calibration circuit.

18 Claims, 15 Drawing Sheets

(56) References Cited

U.S. PATENT DOCUMENTS

| | | | |
|---|---|---|---|
| 2013/0023776 A1 | 1/2013 | Olde et al. | |
| 2014/0128691 A1 | 5/2014 | Olivier | |
| 2015/0335284 A1 | 11/2015 | Nuovo et al. | |
| 2015/0358438 A1 | 12/2015 | Kim et al. | |
| 2016/0103985 A1 | 4/2016 | Shim et al. | |
| 2017/0055859 A1 | 3/2017 | Hsiao et al. | |
| 2017/0172435 A1* | 6/2017 | Presura .............. | A61B 5/02416 |
| 2018/0116532 A1* | 5/2018 | Han ........................ | G06F 1/163 |
| 2019/0200917 A1 | 7/2019 | Murphy et al. | |
| 2020/0221962 A1 | 7/2020 | Matsumoto | |

FOREIGN PATENT DOCUMENTS

| | | | | |
|---|---|---|---|---|
| JP | 2016131796 A | * | 7/2016 | |
| JP | 2017-507724 A | | 3/2017 | |
| JP | 2019-24602 A | | 2/2019 | |
| KR | 10-2015-0140136 A | | 12/2015 | |
| KR | 10-2016-0041553 A | | 4/2016 | |
| KR | 10-2016-0075866 A | | 6/2016 | |
| KR | 10-2017-0008216 A | | 1/2017 | |
| KR | 10-2017-0033755 A | | 3/2017 | |
| KR | 10-2018-0046762 A | | 5/2018 | |
| KR | 10-1978552 B1 | | 8/2019 | |
| WO | 2017025775 A1 | | 2/2017 | |

OTHER PUBLICATIONS

Webster, J.G. (ed.), Design of pulse oximeters, IOP Publishing.
Korean Office Action dated May 12, 2025.
Communication issued on Jan. 16, 2026 by the Korean Ministry of Intellectual Property (MOIP) in Korean Patent Application No. 10-2020-0078155.

\* cited by examiner

1

METHOD FOR CALIBRATING EXTERNAL LIGHT FOR BIO-SIGNAL MEASUREMENT, AND ELECTRONIC DEVICE AND STORAGE MEDIUM THEREFOR

CROSS-REFERENCE TO RELATED APPLICATION(S)

This application is a continuation of International Application No. PCT/KR2021/004704 (published as WO2021/261725), filed on Apr. 14, 2021, designating the United States, in the Korean Intellectual Property Receiving Office, and claiming priority to Korean Patent Application KR 10-2020-0078155 filed on Jun. 26, 2020 in the Korean Intellectual Property Office, the disclosures of which are all incorporated by reference herein in their entireties.

BACKGROUND

1. Field

Certain embodiments relate to an external light calibration method for biometric signal measurement, an electronic device and storage medium therefor.

2. Description of Related Art

An electronic device may include various sensors capable of sensing a user's biometric signals and provide various health-care functions. For example, there may be various types of biometric signals, including, but not limited to electrical signals, such as electrocardiography (ECG) and electromyogram (EMG), physical signals, such as blood pressure, body temperature, and photoplethysmogram (PPG), and composition-related signals, such as blood glucose level, oxygen saturation, and body composition.

The optical heart rate measurement method can be performed to measure changes in the change rate of absorption or transmittance for an internal light source, by using a photodiode, which is a photoelectronic conversion element.

However, the watch-type wearable device does not remain in tight contact with the user's wrist. Therefore, external light (such as sunlight or indoor light) enters through a gap between the device and the wrist. Due to such wearable device structure, motion causes the photodiode to detect light from the internal light source, as well as the light from the outside. The light from the outside causes noise in the measurement.

In particular, since the optical heart rate measurement is a type of measurement using the reflection of the light that is radiated to the surface of the human body (which may also be referred to as light output (or scattered) from the human body (or the skin of the human body)), only detection of the reflected light signal may be of significance. However, if noise is caused due to introduction of external light, the output signal from the PPG sensor may severely fluctuate. This causes unstable acquisition of the biometric signal and resultant deterioration of accuracy and reliability in steady biometric signal measurement.

Thus, it would be desirable to prevent performance deterioration resulting from introduction of external light occurring while the wearable electronic device is worn.

SUMMARY

According to certain embodiments, a wearable electronic device, comprises: at least one light receiving unit; at least one light emitting unit; an external light calibration circuit; and a processor electrically connected with the at least one light receiving unit, at least one light emitting unit, and the external light calibration circuit, wherein the processor is configured to: control the at least one light emitting unit to radiate light during first periods, and not emit light during second periods, and detect light through the at least one light receiving unit during the second periods, and controlling the external light calibration circuit to provide an input to the at least one light receiving unit during first periods, based on the light detected during the second periods; and wherein during the first periods the at least one light receiving unit provides an output based on light received, and the input from the external light calibration circuit.

According to certain embodiments, a method for calibrating external light for biometric signal measurement in a wearable electronic device, comprises: radiating light with at least one light emitting unit during first periods and not radiating light during second periods; detecting a light signal output by at least one light receiving unit during the second periods; and providing an input to the at least one light receiving unit during the first periods by an external light calibration circuit, wherein the input is based on the detected light signal; provides an output during the first periods based on light received and the input by the at least one light emitting unit.

DETAILED DESCRIPTION

Certain embodiments remove the external light component from the measurement by calibrating for external light that is introduced due to various issues with the measurement environment when measuring the biometric signal and thus allow for stable detection of biometric signals alone.

In certain embodiments, it is possible to prevent performance deterioration of biometric signal measurement due to external light introduced while the watch-type wearable electronic device is worn in a loose contact state.

According to certain embodiments, it is possible to minimize data loss even with sudden introduction of external light by performing real-time calibration upon the optical heart rate measurement.

According to certain embodiments, it is possible to minimize, if not eliminate, the difference in DC component for external light upon optical heart rate measurement and to maintain signal to noise ratio (SNR). This enables acquisition of reliable data and accurate measurement.

The terms as used herein are provided merely to describe some embodiments thereof, but not to limit the scope of other embodiments of the present disclosure. It is to be understood that the singular forms "a," "an," and "the" include plural references unless the context clearly dictates otherwise. All terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the present disclosure.

Figure 1A:
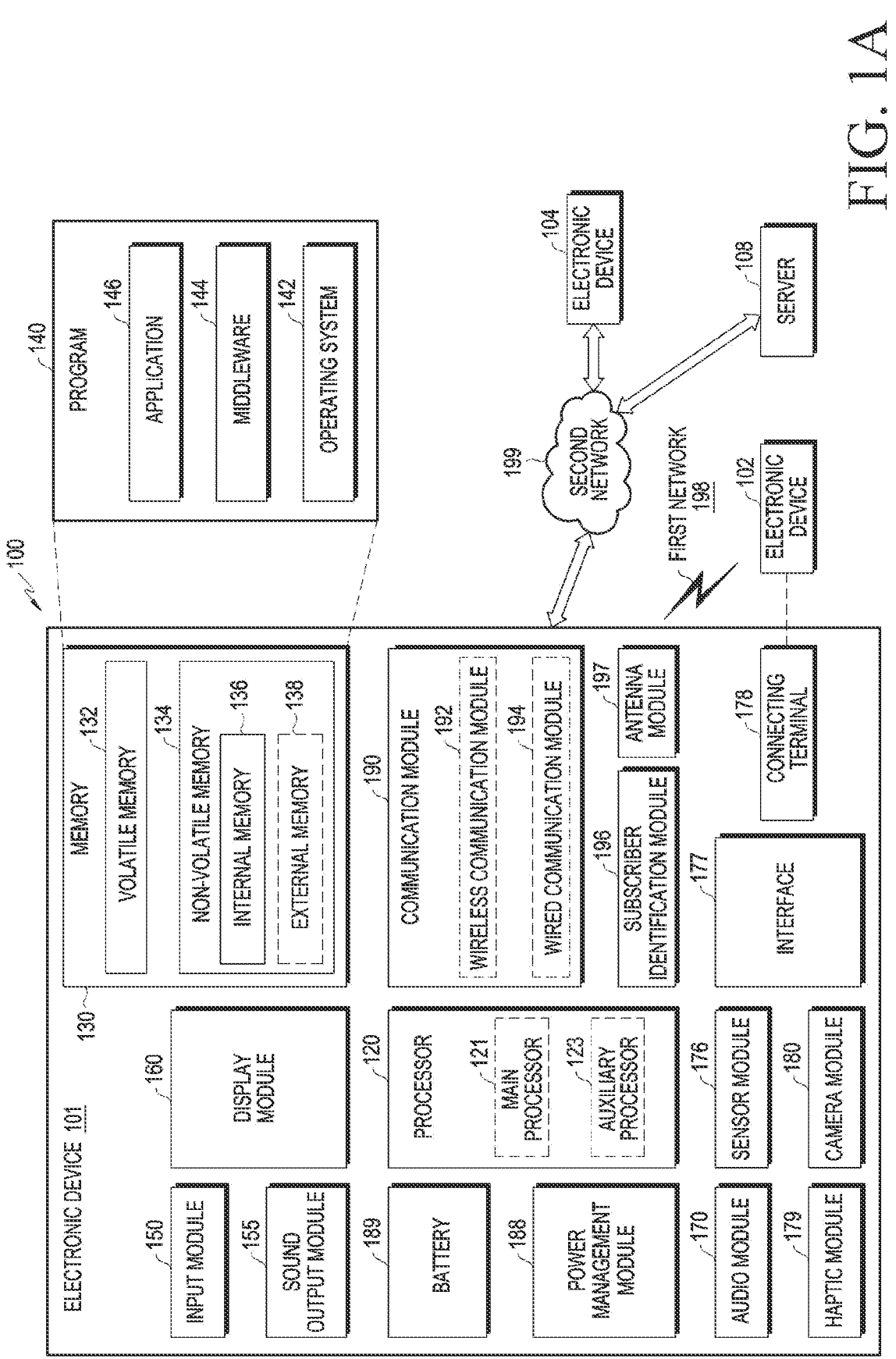
FIG. 1A is a block diagram illustrating an electronic device in a network environment according to an embodiment.
Figures 1B, 1C:
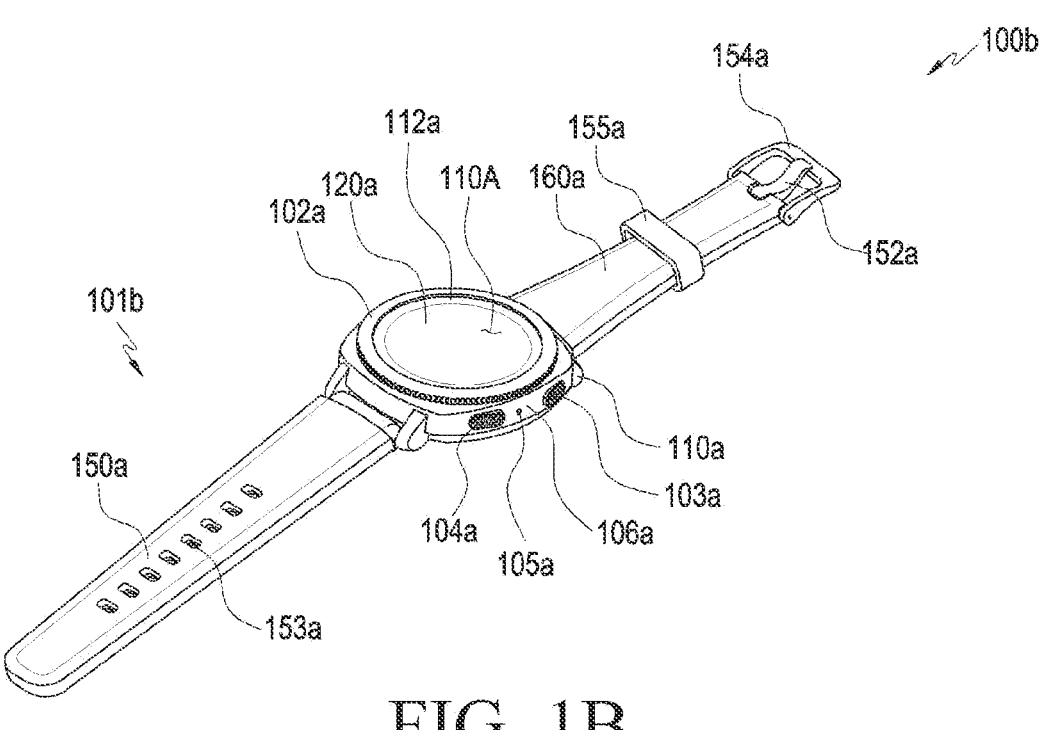
FIG. 1B is a front perspective view illustrating an electronic device according to an embodiment.
FIG. 1C is a rear perspective view illustrating an electronic device as shown in FIG. 1B.
Figure 1D:
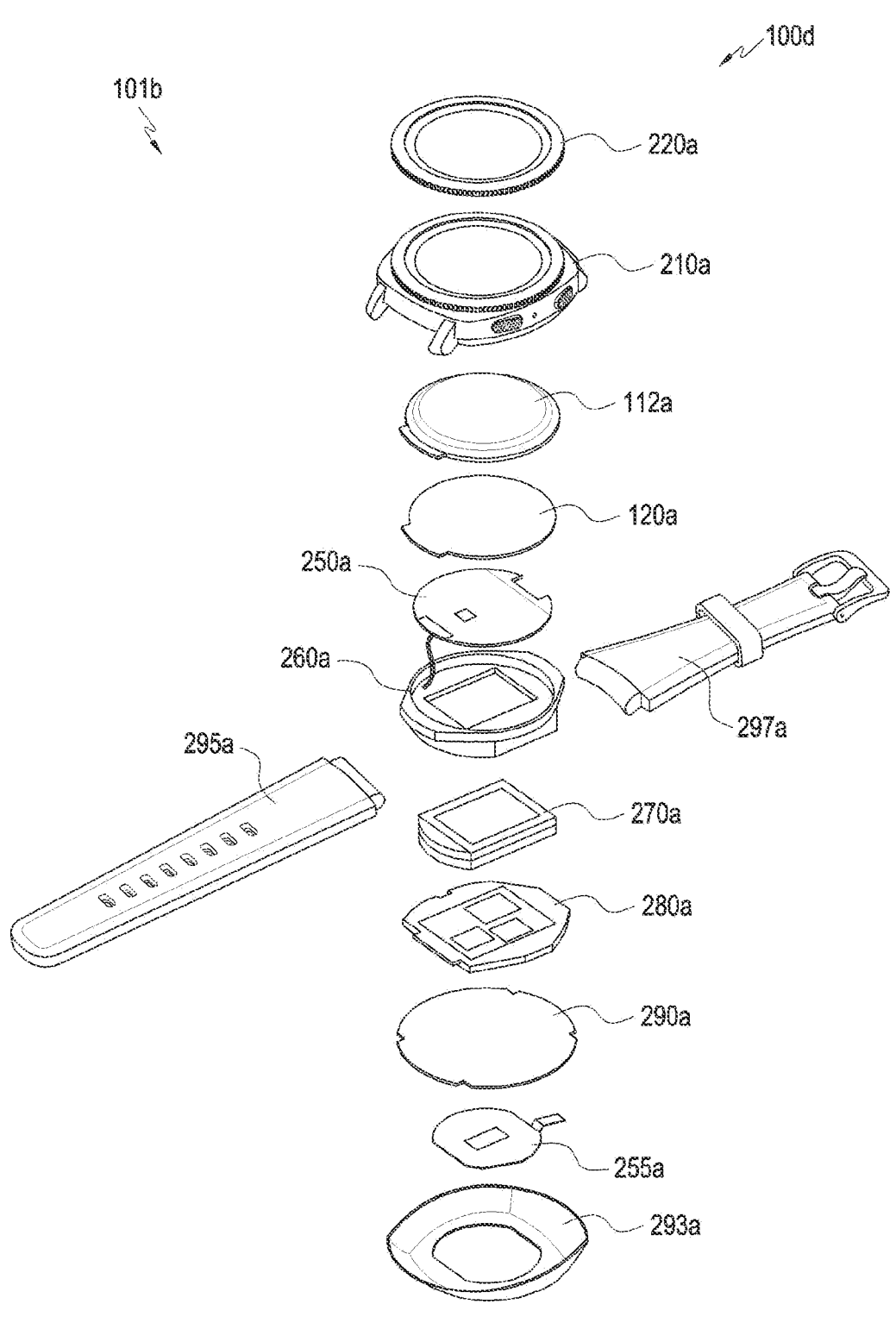
FIG. 1D is an exploded perspective view illustrating an electronic device as shown in FIG. 1B.

This disclosure will begin with a functional description of an electronic device 101 in FIG. 1A. FIGS. 1B and 1C describe the housing of an electronic device 101b, such as a wearable electronic device. A wearable electronic device can include, among other things, a smartwatch. FIG. 1B describes the front of the electronic device 101b. FIG. 1C describes the rear of the electronic device 101b. FIG. 1D discloses an exploded view of an electronic device 101b.

Electronic Device

FIG. 1A is a block diagram illustrating an electronic device 101 in a network environment 100a according to certain embodiments. Referring to FIG. 1A, the electronic device 101 in the network environment 100a may communicate with an electronic device 102 via a first network 198 (e.g., a short-range wireless communication network), or an electronic device 104 or a server 108 via a second network 199 (e.g., a long-range wireless communication network). The electronic device 101 may communicate with the electronic device 104 via the server 108. The electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one (e.g., the display module 160 or the camera module 180) of the components may be omitted from the electronic device 101, or one or more other components may be added in the electronic device 101. According to an embodiment, some (e.g., the sensor module 176, the camera module 180, or the antenna module 197) of the components may be integrated into a single component (e.g., the display module 160). The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. The processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be configured to use lower power than the main processor 121 or to be specified for a designated function. The auxiliary processor 123 may be implemented as separate from, or as part of the main processor 121.

The term processor shall be understood to refer to both the singular and plural contexts in this document.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). The auxiliary processor 123 (e.g., an image signal processor or a communication processor) may be implemented as part of another component (e.g., the camera module 180 or the communication module 190) functionally related to the auxiliary processor 123.

The auxiliary processor 123 (e.g., the neural processing unit) may include a hardware structure specified for artificial intelligence model processing. The artificial intelligence model may be generated via machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by other component (e.g., the processor 120) of the electronic device 101, from the outside (e.g., a user) of the electronic device 101. The input module 150 may include, for example, a microphone, a mouse, a keyboard, keys (e.g., buttons), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. The receiver may be implemented as separate from, or as part of the speaker.

The display module 160 may visually provide information to the outside (e.g., a user) of the electronic device 101. The display 160 may include, for example, a display, a hologram device, or a projector and control circuitry to control a corresponding one of the display, hologram device, and projector. The display 160 may include a touch sensor configured to detect a touch, or a pressure sensor configured to measure the intensity of a force generated by the touch.

The audio module 170 may convert a sound into an electrical signal and vice versa. The audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. The sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. The interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). The connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. The haptic module 179 may include, for example, a motor, a piezoelectric element, or an electric stimulator.

The camera module 180 may capture a still image or moving images. The camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. The battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. The communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via a first network 198 (e.g., a short-range communication network, such as Bluetooth™, wireless-fidelity (Wi-Fi) direct, or infrared data association (IrDA)) or a second network 199 (e.g., a long-range communication network, such as a legacy cellular network, a 5G network, a next-generation communication network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 192 may identify or authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). The wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of Ims or less) for implementing URLLC.

The antenna module 197 may transmit or receive a signal or power to or from the outside (e.g., the external electronic device). The antenna module may include an antenna including a radiator formed of a conductor or conductive pattern formed on a substrate (e.g., a printed circuit board (PCB)). The antenna module 197 may include a plurality of antennas (e.g., an antenna array). In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment, other parts (e.g., radio frequency integrated circuit (RFIC)) than the radiator may be further formed as part of the antenna module 197.

According to certain embodiments, the antenna module 197 may form a mmWave antenna module. The mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. The external electronic devices 102 or 104 each may be a device of the same or a different type from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an Internet-of-things (IoT) device. The server 108 may be an intelligent server using machine learning and/or a neural network. The external electronic device 104 or the server 108 may be included in the second network 199. The electronic device 101 may be applied to intelligent services (e.g., smart home, smart city, smart car, or healthcare) based on 5G communication technology or IoT-related technology.

The sensor module 176 can include a PPG sensor for taking cardio measurements. A PPG sensor can include a light emitting diode (LED) and a photodiode. The light emitting diode can radiate light to the user's body. The user's body can reflect light. The photodiode can detect the light reflected by the user's body. Based on the light detected by the photodiode, the electronic device 101 can provide various health related services.

However, additional light, such as indoor light, or sunlight, may also be detected by the photodiode. The foregoing results in a noise component to the optical heart rate measurements.

Accordingly, in certain embodiments, the effects of indoor light and sunlight are minimized, if not eliminated by performing real-time calibration upon the optical heart rate measurement.

Housing

FIG. 1B is a front perspective view 100b illustrating an electronic device according to an embodiment. FIG. 1C is a rear perspective view 100c illustrating an electronic device as shown in FIG. 1B. The electronic device 101b can be wearable and include wearing members 150a, 160a, such as wrist straps, to fasten the electronic device 101b to the body.

Moreover, the electronic device 101b can include a PPG sensor 165b. The PPG sensor 165b can use LEDS to radiate light towards the user's body and the user's body reflects the light. The reflected light is detected by photodiode(s). Additionally, the wearing members 150a and 160a hold the electronic device 101b, such that the PPG sensor 165b is in close proximity to the user's body.

However, it may still be possible for external light (indoor light, or sun light) to also be detected by the photodiode, thereby introducing a noise component to the biometric signal. Certain embodiments minimize, if not eliminate, the influence of external light.

Referring to FIGS. 1B and 1C, The electronic device 101b (e.g., the electronic device 101 of FIG. 1A) may include a housing 110a including a first surface (or front surface) 110A, a second surface (or rear surface) 110B, and a side surface 110C surrounding the space between the first surface 110A and the second surface 110B and wearing members 150a and 160a connected to at least part of the housing 110a and configured to allow the electronic device 101b to be detachably worn on the user's body portion (e.g., his wrist or ankle). According to another embodiment (not shown), the housing may denote a structure forming part of the first surface 110A, the second surface 110B, and the side surfaces 110C of FIGS. 1B and 1C. At least part of the first surface 110A may have a substantially transparent front plate 112a (e.g., a glass plate or polymer plate including various coat layers). The second surface 110B may be formed of a substantially opaque rear plate 107a. When the electronic device 101b includes a sensor module 165 disposed on the second surface 110B, the rear plate 107a may at least partially include a transparent region.

The rear plate 107a may be formed of, e.g., laminated or colored glass, ceramic, polymer, metal (e.g., aluminum, stainless steel (STS), or magnesium), or a combination of at least two thereof. The side surface 110C may be formed by a side bezel structure (or a "side member") 106a that couples to the front plate 112a and the rear plate 107a and includes a metal and/or polymer. The rear plate 107a and the side bezel structure 106a may be integrally formed together and include the same material (e.g., a metal, such as aluminum). The wearing members 150a and 160a may be formed of various materials in various shapes. A uni-body structure or multiple unit links which is flexible may be formed of fabric, leather, rubber, urethane, metal, ceramic, or a combination of at least two thereof.

The electronic device 101b may include at least one or more of a display 120a (refer to FIG. 1D), audio modules 105a and 108a, a sensor module 165, key input devices 102a, 103a, and 104a, and a connector hole 109a. The electronic device 101b may exclude at least one (e.g., the key input devices 102a, 103a, and 104a, connector hole 109a, or sensor module 165) of the components or may add other components.

The electronic device 101b may include a plurality of electrodes for measuring a biometric signal. At least one of the plurality of electrodes may be placed in at least one of the position of the key input device 102a, 103a, or 104a, the position of the bezel 106a, or the position of the display 120a or the housing 110a. Among the key input devices, the wheel key 102a may include a rotary bezel.

The display 120a may be exposed through a substantial portion of, e.g., the front plate 112a. The display 120a may have a shape corresponding to the shape of the front plate 112a, e.g., a circle, ellipse, or polygon. The display 120a may be coupled with, or disposed adjacent, a touch detection circuit, a pressure sensor capable of measuring the strength (pressure) of touches, and/or fingerprint sensor.

The display 120a may include at least one transparent electrode for measuring biometric signals among the plurality of electrodes for measuring biometric signals.

The audio modules 105a and 108a may include a microphone hole 105a and a speaker hole 108a. The microphone hole 105a may have a microphone inside to obtain external sounds. There may be a plurality of microphones to be able to detect the direction of a sound. The speaker hole 108a may be used for an external speaker or a receiver for phone talks. According to an embodiment, a speaker may be included without the speaker hole (e.g., a piezo speaker).

The sensor module 165 may generate an electrical signal or data value corresponding to an internal operating state or external environmental state of the electronic device 101b. The sensor module 165, e.g., a biometric sensor module (e.g., an HRM sensor) placed on the second surface 110B of the housing 110a, may include an electrocardiogram (ECG) sensor 165a including at least two electrodes a1 and a2 for ECG measurement and a photoplethysmogram (PPG) sensor 165b for heartrate measurement. The electronic device 101b may further include sensor modules not shown, e.g., at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The key input devices 102a, 103a, and 104a may include a wheel key 102a disposed on the first surface 110A of the housing 110a to be rotatable in at least one direction and/or side key buttons 103a and 104a disposed on the side surface 110C of the housing 110a. The wheel key 102a may have a shape corresponding to the shape of the front plate 112a. The electronic device 101b may exclude all or some of the above-mentioned key input devices 102a, 103a, and 104a and the excluded key input devices 102a, 103a, and 104a may be implemented in other forms, e.g., as soft keys on the display 120a. The connector hole 109a may receive a connector (e.g., a universal serial bus (USB) connector) for transmitting and receiving power and/or data to/from an external electronic device. Another connector hole (not shown) may be included for receiving a connector for transmitting and receiving audio signals to/from the external electronic device. The electronic device 101b may further include a connector cover (not shown) to cover at least part of, e.g., the connector hole 109a and preventing undesirable materials from entering the connector hole.

The wearing members 150a and 160a may detachably be fastened to at least portions of the housing 110a via locking members 151a and 161a. The locking members 151a and 161a may include components or parts for coupling, such as pogo pins, and, according to an embodiment, may be replaced with protrusions or recesses formed on/in the wearing members 150a and 160a. For example, the wearing members 150a and 160a may be coupled in such a manner as to be fitted into or over the recesses or protrusions formed on the housing 110. The wearing members 150a and 160a may include one or more of a fixing member 152a, fixing member coupling holes 153a, a band guide member 154a, and a band fixing ring 155a.

The fixing member 152a may be configured to allow the housing 110a and the wearing members 150a and 160a to be fastened to the user's body portion (e.g., wrist or ankle). The fixing member coupling holes 153a may fasten the housing 110a and the wearing members 150a and 160a to the user's body portion, corresponding to the fixing member 152a. The band guide member 154a may be configured to restrict movement of the fixing member 152a to a certain range when the fixing member 152a fits into one of the fixing member coupling holes 153a, thereby allowing the wearing members 150a and 160a to be tightly fastened onto the user's body portion. The band fixing ring 155a may limit the range of movement of the wearing members 150a and 160a, with the fixing member 152a fitted into one of the fixing member coupling holes 153a.

FIG. 1D is an exploded perspective view 100d illustrating the electronic device 101b of FIG. 1B.

Referring to FIG. 1D, an electronic device 101b (e.g., the electronic device 101 of FIG. 1A) may include a side bezel structure 210a, a wheel key 220a, a front plate 112a, a display 120a, a first antenna 250a, a second antenna 255a, a supporting member 260a (e.g., a bracket), a battery 270a, a printed circuit board 280a, a sealing member 290a, a rear plate 293a, and wearing members 295a and 297a. At least one of the components of the electronic device 101b may be the same or similar to at least one of the components of the electronic device 101b of FIG. 1A or 1C and no duplicate description is made below. The supporting member 260a may be disposed inside the electronic device 101b to be connected with the side bezel structure 210a or integrated with the side bezel structure 210a. The supporting member 260a may be formed of, e.g., a metal and/or non-metallic material (e.g., polymer). The display 120a may be joined onto one surface of the supporting member 260a, and the printed circuit board 280a may be joined onto the opposite surface of the supporting member 260a. A processor, memory, and/or interface may be mounted on the printed circuit board 280a. The processor may include one or more of, e.g., a central processing unit, an application processor, a graphic processing unit (GPU), a sensor processor, or a communication processor.

The memory may include, e.g., a volatile or non-volatile memory. The interface may include, e.g., a high definition multimedia interface (HDMI), a universal serial bus (USB) interface, a secure digital (SD) card interface, and/or an audio interface. The interface may electrically or physically connect, e.g., the electronic device 101b with an external electronic device and may include a USB connector, an SD card/multimedia card (MMC) connector, or an audio connector.

The battery 270a may be a device for supplying power to at least one component of the electronic device 101b. The battery 270a may include, e.g., a primary cell which is not rechargeable, a secondary cell which is rechargeable, or a fuel cell. At least a portion of the battery 270a may be disposed on substantially the same plane as the printed circuit board 280a. The battery 270a may be integrally or detachably disposed inside the electronic device 101b.

The first antenna 250a may be disposed between the display 120a and the supporting member 260a. The first antenna 250a may include, e.g., a near-field communication (NFC) antenna, a wireless charging antenna, and/or a magnetic secure transmission (MST) antenna. The first antenna 250a may perform short-range communication with an external device, wirelessly transmit/receive power necessary for charging, or transmit magnetic-based signals including payment data or short-range communication signals. According to an embodiment, an antenna structure may be formed by a portion or combination of the side bezel structure 210a and/or the supporting member 260a.

The second circuit board 255a may be disposed between the circuit board 280a and the rear plate 293a. The second circuit board 255a may include an antenna, e.g., a near-field communication (NFC) antenna, a wireless charging antenna, and/or a magnetic secure transmission (MST) antenna. The second circuit board 255a may perform short-range communication with an external device, wirelessly transmit/receive power necessary for charging, or transmit magnetic-based signals including payment data or short-range communication signals. According to an embodiment, an antenna structure may be formed by a portion or combination of the side bezel structure 210a and/or the rear plate 293a. According to an embodiment, when the electronic device 101b (e.g., the electronic device 101b of FIG. 1B or 1C) includes a sensor module (e.g., the sensor module 165 of FIG. 1B), a sensor element (e.g., a photoelectric conversion element or electrode pad) separate from the second circuit board 255a or the sensor circuit disposed on the second circuit board 255a may be disposed. For example, an electronic component provided as the sensor module 165 may be disposed between the circuit board 280a and the rear plate 293a.

The sealing member 290a may be positioned between the side bezel structure 210a and the rear plate 293a. The sealing member 290a may be configured to block moisture or foreign bodies that may enter the space surrounded by the side bezel structure 210a and the rear plate 293a, from the outside.

According to certain embodiments described below, examples of measurable biometric signals may include electrical signals, such as electrocardiogram (ECG), electroencephalography (EEG), and electromyography (EMG), physical signals, such as blood pressure, body temperature, and PPG, and composition-related signals, such as blood glucose level, oxygen saturation, and body composition. However, the measurable biometric signals are not limited thereto. Further, although the description focuses primarily on an example of correcting external light for a PPG signal for optical heartbeat measurement, this is merely for convenience of description, and embodiments are not limited thereto.

PPG Sensor

Figure 2:
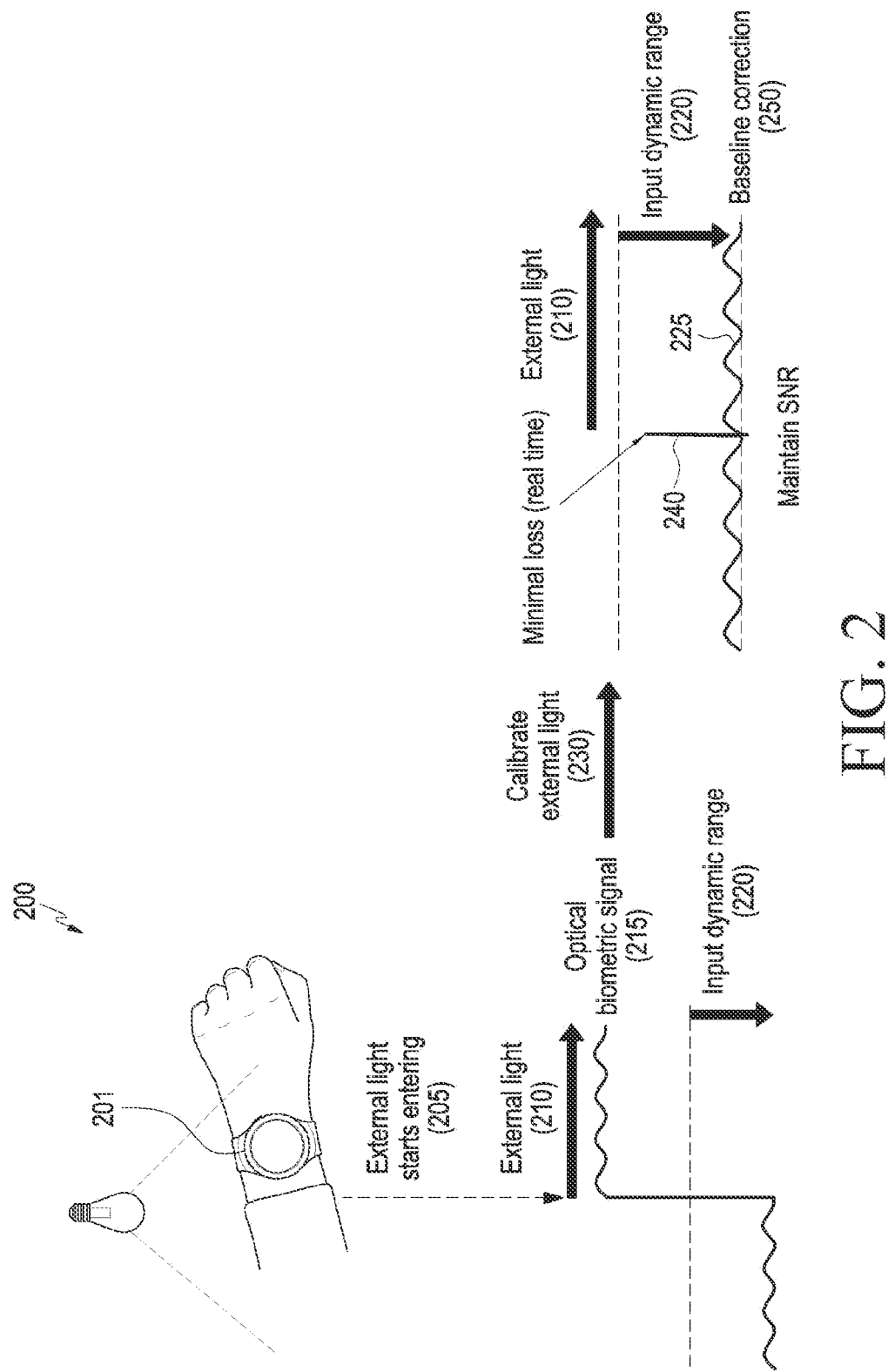
FIG. 2 is a view illustrating changes in obtaining a biometric signal due to introduction of external light according to certain embodiments.

FIG. 2 is a view 200 illustrating changes in obtaining a biometric signal due to introduction of external light according to certain embodiments.

Referring to FIG. 2, biometric signal measurement is performed continuously for 24 hours while the wearable electronic device 201 is worn by the user. Various noises other than the biometric signal may be superposed according to the user's movement and posture while wearing the wearable electronic device 201. The foregoing leads to a higher change of an error in analyzing the biometric signal waveform. For example, as shown in FIG. 2, when external light introduction to the optical biometric signal 215 starts (205), the biometric signal may fall outside of the input dynamic range 220. In this case, if the external noise corresponding to the external light enters the biometric signal, e.g., PPG sensor, of the wearable electronic device 201, it may be difficult to determine whether the light entering the PPG sensor is external light or reflected light. In particular, when falling outside of the input dynamic range 220, the signal may be saturated, rendering it possible to measure the biometric signal.

The wearable electronic device 201 calibrates for external light calibration 230 in realtime at the time of introduction of the external light 210 while measuring the optical biometric signal 215, so that only minimum data loss 240 occurs. Therefore, although the external light 210 may be included in the optical biometric signal 215, the input dynamic range 220 may be stably maintained so that a calibrated optical biometric signal 225 waveform is output as if a baseline calibration 250 operation was performed. Further, according to certain embodiments, although the external light is introduced together, the wearable electronic device 201 may maintain SNR without a difference in DC component for the external light, so that reliable data can be obtained.

A device for processing biometric signals for external light calibration may be a wearable electronic device. The wearable electronic device may include a housing and/or a bezel. The rear surface of the housing, i.e., the rear surface of the wearable electronic device, may contact a body portion (e.g., wrist), and the rear surface may be formed of metal. Sensors for measuring biometric signals may be arranged around the center portion of the rear surface. The arrangement of the sensors is described below with reference to FIG. 4.

A method for processing biometric signals for external light calibration and embodiments of a wearable electronic device are described below in detail with reference to the drawings.

Figure 3:
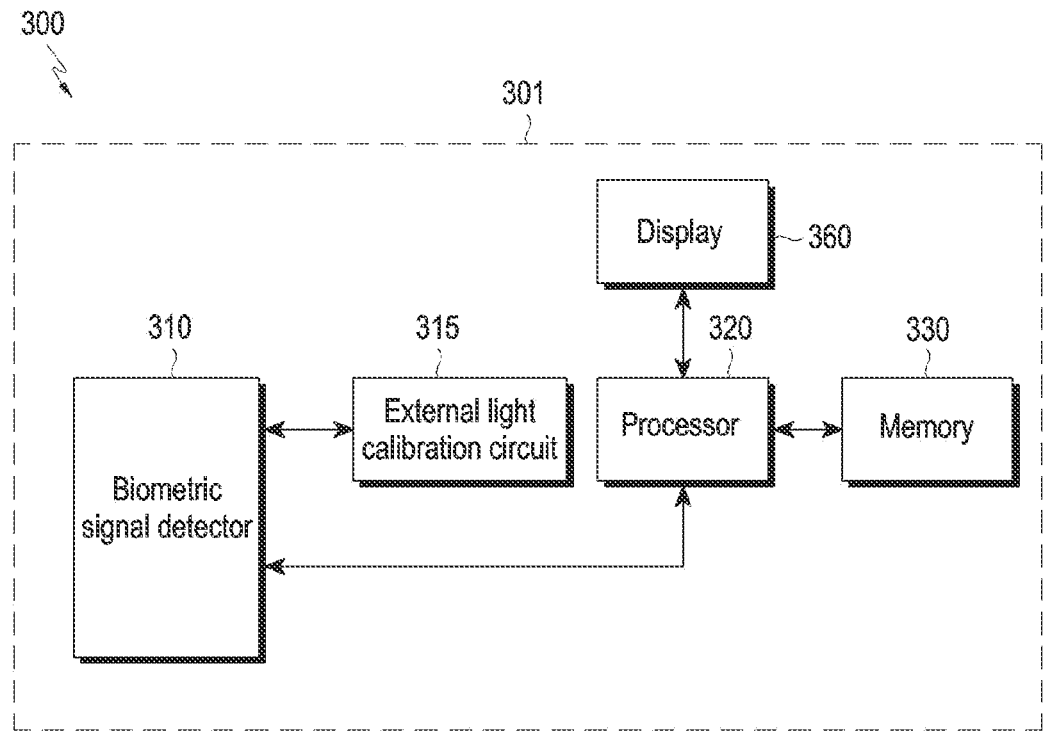
FIG. 3 is a block diagram schematically illustrating a biometric signal processing device for external light calibration according to certain embodiments.

FIG. 3 is a block diagram 300 schematically illustrating a biometric signal processing device for external light calibration according to certain embodiments.

FIG. 3 is a block diagram illustrating an internal configuration of a biometric signal processing device according to an embodiment. The biometric signal processing device may be a wearable electronic device. The biometric signal processing device may be equipped, in the form of a hardware or software module, in an electronic device, such as a wearable electronic device. The biometric signal processing device may be implemented as a stand-alone hardware device in which case it may be used to obtain and analyze various kinds of biometric signals. However, without limitations thereto, various modifications may be made thereto depending on the purposes of utilizing the instant technology.

The biometric light detector 310 receives reflected light as well as external light and outputs an electrical corresponding to the reflected light and external light. The external light calibration circuit 315 detects light from a light receiving unit during when a light emitting unit is not emitting light. As a result, the signal provided by the light receiving unit is an electrical signal corresponding to the external light. The external light calibration circuit 315 can then apply the current with the magnitude corresponding to the extracted external light signal to the input terminal of at least one light receiving unit.

Referring to FIG. 3, a biometric signal processing device 301 may include a biometric signal detector 310, an external light calibration circuit 315, a processor 320, a memory 330, and a display 360. Here, the biometric signal processing device 301 may be a wearable electronic device (e.g., the electronic device 101 of FIG. 1A or the electronic device 101*b* of FIGS. 1B to 1D).

The biometric signal detector 310 may include a plurality of sensors and receive signals for obtaining biometric signals through the plurality of sensors. For example, the plurality of sensors may include biometric sensors, such as an electrocardiogram sensor (hereinafter, ECG sensor), a photoplethysmography sensor (hereinafter, PPG sensor), a heart rate sensor, and a body temperature sensor and, as necessary, may include optionally other various sensors for measuring necessary biometric signals, such as an acceleration sensor but embodiments of the disclosure are not limited thereto.

Among the plurality of sensors, the PPG sensor is a sensor for estimating various biological states based on the characteristics of the body or the blood flow in the body using the characteristics of absorption, scattering, or reflection by the skin tissues of the user's body, obtained by radiating light to the user's body (or user's skin).

It is possible to obtain various biometric information based on heart rate information including the heart rate by using the PPG sensor. For example, if the PPG sensor is used, various wavelengths of light may be radiated and received, so that it is possible to measure the blood saturation of percutaneous oxygen (SpO2), with a plurality of wavelengths of light signals.

If a plurality of sensors including the PPG sensor are used, upon measuring an ECG signal, the acceleration, PPG, and SpO2 may be measured as well. The blood pressure may be measured using the ECG and PPG signals, and sleep apnea may be measured using the acceleration and SpO2 signal. For example, the measurement value from the acceleration sensor may measure the change in the height of the chest during breathing and the user's toss-and-turn. In particular, the SpO2 measurement value is a measurement of the blood oxygen concentration and sleep apnea may be detected by determining whether the SpO2 measurement value reduces.

The biometric signal detector 310 may include at least one light emitting unit (or light emitting element) and at least one light receiving unit (or light receiving element). The sensor including the at least one light emitting unit and the at least one light receiving unit may be referred to as a PPG sensor.

The biometric signal detector 310 may radiate a specific wavelength of light to the user's body through the at least one light emitting unit The at least one light emitting unit may radiate light with a predetermined intensity to the user's body. The wavelength of the radiated light may be varied depending on the object of the measurement or the type of the target component to be analyzed. The at least one light emitting unit may include a light emitting diode (LED) or a laser diode (LD). For example, the at least one light emitting unit may use various wavelength bands, such as green light, red light, blue light, or infrared light, to reduce influence of motion artifacts and may emit light in a manner to simultaneously turn on or alternate several wavelengths.

Further, the biometric signal detector 310 may detect the light reflected or transmitted from the user's body corresponding to the radiated light, through the at least one light receiving unit. The biometric signal detector 310 may output the biometric signal corresponding to the light returning from the user's body through the at least one light receiving unit.

The at least one light receiving unit of the biometric signal detector 310 may receive the light radiated and returning and generate at least one biometric information using the electrical signal into which the light has been converted. The signal may be a PPG signal. The at least one light receiving unit may include a photodiode (PD), a photo transistor, or a charge-coupled device (CCD). As long as it is an element capable of converting a light signal into an electrical signal, the type of the device may not be limited thereto. The structure of at least one light receiving unit may be a reflective-type or a transmissive-type.

The biometric signal detector 310 may receive the current corresponding to the measured PPG signal, convert the measured PPG signal into a digital signal, and transfer the digital signal to the processor 320. The biometric signal detector 310 may perform current-voltage conversion for processing the PPG signal and, before transferring to the processor 320, digitize the output analog voltage signal and transfer the result to the processor 320.

Accordingly, the processor 320 may analyze the biometric signal based on the biometric signal from the biometric signal detector 310. The processor 320 may be the processor 120 of FIG. 1. Or, the processor 320 may be a sensor processor implemented separately from the processor 120 of FIG. 1. For example, the processor 320 may measure an intravascular blood flow that is increased or decreased due to a heartbeat based on the biometric signal collected through at least one light receiving unit and may measure the user's pulse wave based on the measured blood flow. For example, it is possible to obtain information about the user's heart rate and monitor the health condition based on the received heart rate information.

Meanwhile, according to an embodiment, at least one light receiving unit of the biometric signal detector 310 may collect light and convert it into current. If external light is introduced, the signal including the external light together with the reflection light by the internal light source (which may also be referred to as light output (or scattered) from the body (or the skin of the body)) may be output. For example, when the signal output from the biometric signal detector 310 includes the external light signal, the external light calibration circuit 315 may perform a calibration operation for removing the external light signal to obtain only the biometric signal.

The external light calibration circuit 315 may extract or remove a the external light signal from the signal output from the biometric signal detector 310. The external light calibration circuit 315 can then apply the current with the magnitude corresponding to the extracted external light signal to the input terminal of at least one light receiving unit. As a result, the external light calibration unit 315 removes the external light signal.

The external light calibration circuit 315 may use the on/off characteristics of at least one light emitting unit as a method for extracting only the external light signal from the signal output from the biometric signal detector 310.

The processor 320 may remove the external light signal from the biometric signal with the external light calibration circuit 315.

The processor 320 may be electrically connected with the external light calibration circuit 315 and the biometric signal detector 310 and control to radiate light to the user's body (or the user's skin) through the at least one light emitting unit of the biometric signal detector 310.

The at least one light emitting unit can have a first period where the at least one light emitting unit radiates light and a second period where the at least one light emitting unit does not radiate light. In certain embodiments, the first period and second period can be repeated, such that a cycle includes the first period followed by the second period.

The processor 320 may detect the external light signal output through the at least one light receiving unit during a second period, using the external light calibration circuit 315. Accordingly, when the at least one light emitting unit radiates light, the processor can remove the external light signal from the biometric signal provided by the at least one light receiving unit. The first period during which the light is radiated may be a period during which the at least one light emitting unit, e.g., an LED, is on, and the second period during which the light is not radiated may be a period during which the LED is off.

As described above, the signal detected during the period when the LED is off may be regarded as the external light signal since there would be no light reflected by the user's skin. The signal applied at this time may be applied to the external light calibration circuit 315 to extract only the external light signal. The external light signal may be removed from the biometric signal detected during the period when the LED is on, based on the extracted external light signal. For example, during the LED-off period, the output terminal from the biometric signal detector 310 may be switched to connect to the input terminal of the external light calibration circuit 315 and, during the LED-on period, the output terminal from the biometric signal detector 310 may be switched to connect to the input terminal of the processor 320 (or the output terminal from the biometric signal detector 310 does not connect to the input terminal of the external light calibration circuit 315). According to an embodiment, during the LED-on period, the output signal (or calibrated biometric signal) from the biometric signal detector 310 may be converted into a digital signal and be transferred to the processor 320. To that end, analog-digital (AD) conversion may be performed.

The light input at an LED off timing through at least one light receiving unit corresponds to external light, so that if only external light is selectively extracted by performing sampling only at the LED-off timing, it may be known how much external light signal is included in the biometric signal. Here, sampling during the LED-off timing represents an operation for storing the potential for the external light and may differ from sampling to convert the voltage signal into a digital signal. Accordingly, if as large a signal magnitude as the magnitude corresponding to the external light is subtracted, it is possible to obtain only the biometric signal by the internal light source, i.e., the at least one light emitting unit.

The external light calibration circuit 315 may perform the operation of removing external light every LED-off interval but, even at the LED-on timing, perform external light calibration operation in realtime (or continuously).

The external light calibration circuit 315 may extract the external light signal every LED-off timing and, every LED-on timing, perform the external light calibration operation (i.e., the operation of removing the external light signal/component from the biometric signal) using the external light signal extracted at the LED-off timing without extracting the external light signal.

The processor 320 may detect, predict, or analyze the user's health condition based on the biometric signal from the biometric signal detector 310.

The processor 320 may measure the heart rate using the PPG sensor of the biometric signal detector 310. The heart rate is an observation of the number of pumps in the heart for one minute and be used to determine the health condition on ordinary days or exercise state. The processor 320 may determine the stress or tension level by using heart rate variability (HRV) based on the heart rate interval information.

As described above, the processor 320 may analyze the biometric signal and store it in the memory 330 to provide at least one piece of biometric information. Here, the at least one piece of biometric information may be information, such as heart rate, blood pressure, or sleep apnea. Such biometric information may be utilized as basic data for analyzing the user's physical strength or health condition.

The processor 320 may obtain more complex and medical information through a combination with the user's personal information or history information, artificial intelligence (AI), and bigdata. For example, medical information that may be fatal to the user, such as blood pressure, blood glucose, atrial fibrillation, and arrhythmia may also be measured. The information may be measured by a single PPG sensor or may be combined with another sensor or several additional pieces of information to be corrected into more accurate, reliable information. Further, the processor 320 may detect sleep and respiration and may also detect an abnormality, such as sleep apnea, or a gesture based on a change in blood flow according to a hand gesture. Various symptoms, such as blood pressure and sleep apnea, as well as simple heart checkup, may be measured by using various sensors together with the PPG sensor of the biometric signal detector 310, thereby providing a complex health-care function.

According to certain embodiments, the processor 320 may provide a biometric signal in the form of the original signal, where noise, e.g., external light, has been removed, and provide high-accuracy biometric information based on the biometric signal.

The memory 330 may store data (e.g., biometric information) from the biometric signal processing device (or wearable electronic device) 301. The memory 330 may be implemented in substantially the same or similar manner to the memory 130 described above in connection with FIG. 1A. The memory 330 may be implemented as a non-volatile memory.

According to certain embodiments, the display 360 may be implemented in substantially the same or similar manner to the display module 160 described in connection with FIG. 1A. The display 360 may receive at least one piece of biometric information from the processor 320 and visually display the same. For example, the display 360 may display a user interface based on the biometric signal measured upon executing an application for biometric signal measurement (e.g., an ECG application or a health-care application). The display 360 may output a guide screen or abnormal state upon measuring a biometric signal under the control of the processor 320.

Figure 4:
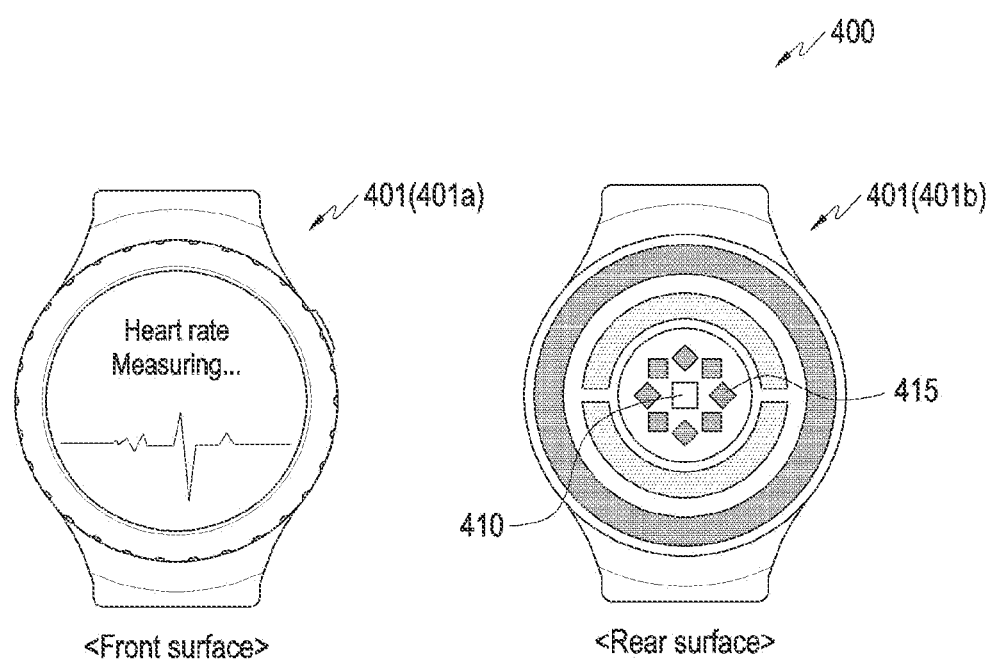
FIG. 4 is a view illustrating an example of placement of a PPG sensor of a wearable electronic device according to certain embodiments.

FIG. 4 is a view 400 illustrating an example of placement of a PPG sensor of a wearable electronic device according to certain embodiments. FIG. 4 illustrates the front surface 401a and the rear surface 401b of the wearable electronic device 401 (e.g., the electronic device 101 of FIG. 1A, the electronic device 101b of FIGS. 1B to 1D, or the biometric signal processing device 301 or wearable electronic device 301 of FIG. 3).

As shown in FIG. 4, a PPG sensor includes at least one light emitting unit 410 and at least one light receiving unit 415. The light emitting unit 410 and the light receiving unit 415 measure the optical biometric signal and may be disposed on the rear surface 401b of the wearable electronic device 401. The at least one light receiving unit 415 may be disposed on the same surface as the at least one light emitting unit 410.

As shown in FIG. 4, the at least one light emitting unit 410 may be positioned in the middle of the rear surface 401b and be constituted of a single element or a plurality of elements. The single element emits the same wavelength band of light. The plurality of elements can emit different wavelength bands of light. Further, although FIG. 4 shows an example in which the at least one light emitting unit 410 is positioned in the middle, it may be disposed outside the light receiving unit 415 considering the positional relationship with the light receiving unit 415. Alternatively, the light emitting unit 410 may be disposed in a position where the influence by the external light is as low as possible, e.g., as inside as possible, considering the situation in which sleep is disturbed in the middle of the night by the nature of the PPG sensor that performs monitoring 24 hours.

Meanwhile, in FIG. 4, the rear surface 401b where the PPG sensor is disposed may be a flat surface or may be formed in a dome shape which is curved to be brought in tight contact with the user's skin (e.g., wrist). For example, since it is advantageous in performance measurement that the at least one light receiving unit 415 collects the light emitted from the at least one light emitting unit 410 as much as possible, more and broader light receiving units 415 may be advantageous. FIG. 4 illustrates a case in which eight light receiving units 415 surround at least one light emitting unit 410 on the rear surface 401b.

Meanwhile, more external light may be introduced when the light receiving units increase in number or area or when formed in a curved shape than flat. According to certain embodiments, since the external light may be removed, it is possible to diversify the design regardless of how much external light is introduced, thus expanding the design development range for wearable electronic devices. Further, although an example in which the rear surface 401b is flat or convex has been described in connection with FIG. 4, the shape may not be limited thereto.

Figure 5:
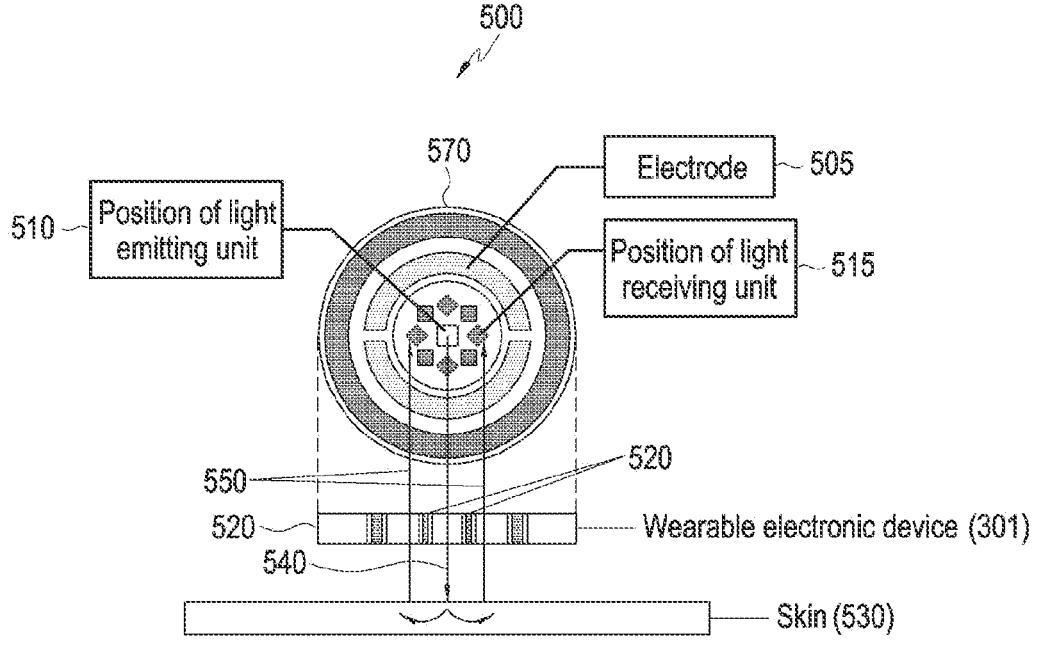
FIG. 5 is a view illustrating a structure of a PPG sensor according to certain embodiments.

FIG. 5 is a view illustrating a structure 500 of a PPG sensor according to certain embodiments.

Referring to FIG. 5, a plurality of sensors are included on the rear surface of a wearable electronic device (e.g., the biometric signal processing device 301 of FIG. 3). Among the plurality of sensors is a PPG sensor, which is an optical sensor. The optical sensor may be used to measure PPG signals (or data).

FIG. 5 describes the rear surface 570 of the wearable electronic device 301 and the vertically cross-section 560 of the PPG sensor-side end of the wearable electronic device 301. As shown in FIG. 5, a structure divided by a barrier rib 520 may be formed according to the position 515 of at least one light receiving unit of the PPG sensor of the wearable electronic device and the position 510 of at least one light emitting unit, and the barrier rib 520 structure may be used as a passage for measuring the PPG signal.

According to certain embodiments, other various sensors than the PPG sensor may be disposed on the rear surface of the wearable electronic device 301. At least one electrode 505 may be included on the rear surface of the wearable electronic device 301. Further, according to certain embodiments, at least one light emitting unit (e.g., LED) and at least one light receiving unit (e.g., PD) may be disposed in the main body (e.g., on the PCB) of the wearable electronic device 301. On the rear surface 570 of the wearable electronic device 301, a first position (e.g., light emitting unit position) 510 corresponding to at least one light emitting unit (e.g., LED) which is hidden and invisible and a second position (e.g., light receiving unit position) 515 corresponding to at least one light receiving unit (e.g., PD) may be marked. For example, in practice, the light emitting unit position 510 and the light receiving unit position 515 may be portions of the glass, and at least one light emitting unit and at least one light receiving unit may be formed inside the wearable electronic device of the light emitting unit position 510 and the light receiving unit position 515. The glass may be colored in ink so that the at least one light emitting unit and at least one light receiving unit disposed in the wearable electronic device 301 are invisible.

The at least one light emitting unit may be disposed inside, in the position corresponding to the light emitting unit position 510, and the at least one light receiving unit may be disposed inside, in the position corresponding to the light receiving unit position 515. An opaque optical shield (or barrier rib) 520 may be formed to surround the side portion extending from the at least one light emitting unit and at least one light receiving unit to the surface exposed to the outside of the rear surface of the wearable electronic device 301 Such opaque optical shield may be referred to as a barrier rib. The barrier rib structure may have a structure that prevents the light emitted from the at least one light emitting unit from entering the at least one light receiving unit after being diffracted or reflected by the internal structure. The barrier rib structure may be not only a passage for guiding the light emission path of the at least one light emitting unit but also a passage for receiving the light reflected from the user's skin.

According to certain embodiments, the wearable electronic device 301 may collect the PPG sensor through the middle hole divided by the barrier rib 520 while simultaneously measuring the ECG signal through at least one electrode 505. According to certain embodiments, if measurement commences, the light from the at least one light emitting unit (LED) 510 may be oriented to the user's body, e.g., the user's skin 530, and the reflected light may have a state modulated by the blood flow under the skin 530. The reflected light may be collected (550) by at least one light receiving unit (PD) 515 via the passage formed by the barrier structure.

Figure 6:
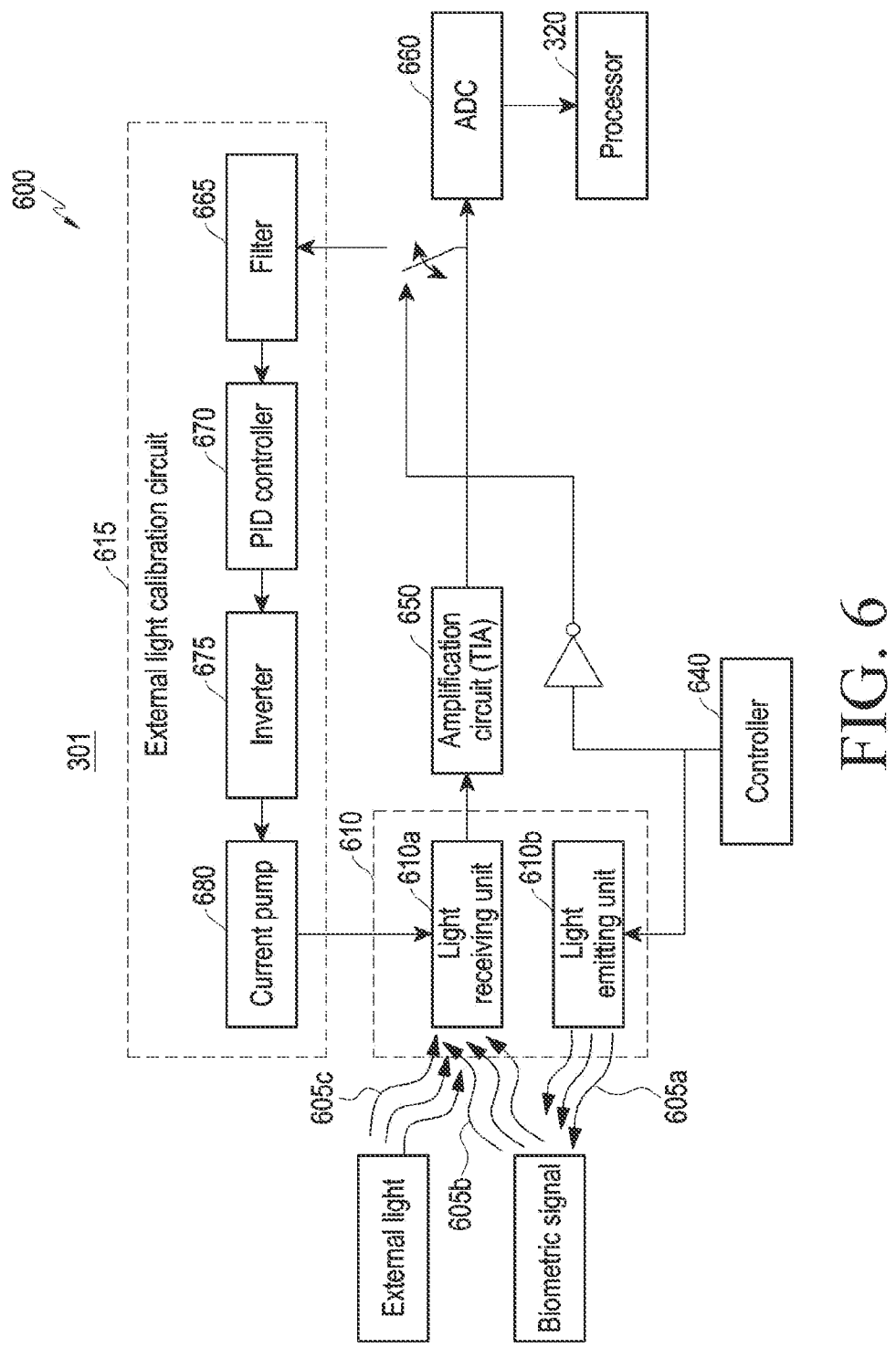
FIG. 6 is a view illustrating an example of a biometric signal processing circuit for external light calibration in a wearable electronic device according to certain embodiments.

FIG. 6 is a view 600 illustrating an example of a biometric signal processing circuit for external light calibration in a wearable electronic device according to certain embodiments.

FIG. 6 illustrates a detailed structure of the biometric signal detector 310 and the external light calibration circuit 315 for biometric signal processing of FIG. 3. For ease of description, an example is described below in which the biometric signal processing device is a wearable electronic device.

The light emitting unit 610b has a first period when the light emitting unit 610b emits light, and a second period when the light emitting unit 610b does not emit light. In certain embodiments, the first period and second period can be repeating, thereby resulting in alternating periods of light, and no light. When the light emitting unit 610b does not emit light, the light receiving unit 610a receives only the external light 605c. The light receiving unit 610a converts the external light 605c to an external light signal. The external light signal can be provided as an input to the external light calibration unit 615. The external light calibration unit 615 provides an input to the light receiving unit 610a during a subsequent period when the light emitting unit 610b emits light.

When the light emitting unit 610b emits light, the light is reflected (reflected light 605b) by the user's skin. However, the light receiving unit 610a receives both the reflected light 605b, and external light 605c. The light receiving unit 610a can use the input to provide an electronic signal that only corresponds to the light that is reflected.

A controller 640 controls a switch that connects the output of the light receiving unit 610a to the external light calibration circuit 615, during the second period (when light is not emitted), but connects to and ADC 660 during the first period (light is emitted).

As shown in FIG. 6, the wearable electronic device 301 may include a PPG sensor 610, an amplification circuit 650, an external light calibration circuit 615, and an analog-to-digital converter (ADC) 660. The biometric signal detector 310 of FIG. 3 may include the PPG sensor 610 and the amplification circuit 650. The output from the biometric signal detector 310 may be converted into a digital signal through the ADC 660 before transferred to the processor 320 and be output to the processor 320. In other words, the output from the ADC 660 may be input to the processor 320. The ADC 660 may further be included in the biometric signal detector 310 so that the output from the biometric signal detector 310 is transferred to the processor 320 or be alternatively implemented separately between the biometric signal detector 310 and the processor 320.

Meanwhile, as shown in FIG. 6, the PPG sensor 610 may include at least one light receiving unit 610a and at least one light emitting unit 610b. Described below is an example in which the at least one light receiving unit 610a is a PPD, and the at least one light emitting unit 610b is an LED.

As shown in FIG. 6, the wearable electronic device 301 may further include a controller 640 to control the on/off operation of the at least one light emitting unit 610b. Alternatively, the on/off operation of the at least one light emitting unit 610b may be controlled under the control of a processor (e.g., the processor 320 of FIG. 3). At the on-time of the at least one light emitting unit 610b, the output terminal of the amplification circuit 650 may be connected to the input terminal of the ADC 660 under the control of the controller 640 (or the output terminal of the amplification circuit 650 may not be connected to the input terminal of the external light calibration circuit 615). Accordingly, the reflected light 605b by the light 605a in the on state of the at least one light emitting unit 610b may be received through at least one light receiving unit 610a, converted into a voltage through the amplification circuit 650, and output to the ADC 660.

The amplification circuit 650 may include a transimpedance amplifier (TIA). The amplification circuit 650 may convert the current signal corresponding to the reflected light output from the at least one light receiving unit 610a into a voltage signal. The current signal transferred to the amplification circuit 650 may be a current signal generated by an optical signal (e.g., reflected light 605b) input to the at least one light receiving unit 610a.

Meanwhile, when light is received through the at least one light receiving unit 610a in the off state of the at least one light emitting unit 610b, the light is not the reflected light 605b by the light radiated by the at least one light emitting unit 610b but may correspond to the external light 605c. Accordingly, in the off state of the at least one light emitting unit 610b, the current component output through the at least one light receiving unit 610a may correspond to external light, so that only the external light component may be extracted, and the external light calibration operation may be performed.

To that end, at the off time of the at least one light emitting unit 610b, the output terminal of the amplification circuit 650 of the biometric signal detector 310 may be connected to the external light calibration circuit 615 under the control of the controller 640. Accordingly, the component corresponding to the external light output through the at least one light receiving unit 610a may be input to the external light calibration circuit 615, and the calibration operation may be performed to remove the component corresponding to the external light from the component output through the at least one light receiving unit 610a.

As described above, the output terminal of the amplification circuit 650 of the biometric signal detector 310 may be connected to the input terminal of the ADC 660 or be selectively connected to the input terminal of the external light calibration circuit 615 according to the on/off time of the at least one light emitting unit 610b. For example, the selective connection may be implemented in a switching manner.

The external light calibration circuit 615 may include a filter 665, a proportion integral derivation (hereinafter 'PID') controller 670, an inverter 675, or a current pump 680.

The external light calibration circuit 615 may be configured to have a feedback structure in which the output terminal of the external light calibration circuit 615 is connected to the input terminal of the at least one light receiving unit 610a, playing a role to remove the current signal corresponding to the external light. The external light calibration circuit 615 may monitor changes in the output terminal of the amplification circuit 650, e.g., changes in voltage and feed back to the input terminal of the at least one light receiving unit 610a according to the monitoring result, removing the current component corresponding to the external light signal from the light signal coming from the at least one light receiving unit 610a.

The output terminal of the external light calibration circuit 615, e.g., the output terminal of the current pump 680, may be connected with the input terminal of the at least one light receiving unit 610a. As described above, as the external light calibration circuit 615 is disposed with a feedback structure which includes the current pump 680 serving to remove the current signal corresponding to the external light at the input terminal of the at least one light receiving unit 610a, realtime monitoring is possible, so that realtime calibration is possible.

For example, it is possible to initially remove the external light component through external light calibration so that no voltage change is made due to influence of the external light over time upon realtime biometric signal measurement. Here, when a voltage change is initially caused due to the external light, processing for obtaining the biometric signal may temporarily be not performed on the signal output through the amplification circuit 650 while external light calibration is performed. Such temporary period may be referred to as a blanking region. If some signals obtained in a certain initial period are disregarded, only biometric signals in the input dynamic range may be obtained although there is sudden introduction of external light, rendering it possible to stably obtain biometric signals. For example, as shown in FIG. 2, only the partial signal 240 corresponding to the blanking region is not processed, so that loss of biometric signal may be minimized, and biometric signals may stably be obtained.

As described above, when the current signal output from the at least one light receiving unit 610a is input to the amplification circuit 650 so that there is a voltage signal output through the amplification circuit 650 in the off period of the at least one light emitting unit 610b during the repeated on/off operation of the at least one light emitting unit 610b, the external light calibration operation may be performed with the voltage signal regarded as the voltage signal corresponding to the external light. In this case, since the voltage output through the amplification circuit 650 is a voltage coming in the off period of the at least one light emitting unit 610b although the magnitude of the voltage falls within, e.g., the input dynamic range 220, the external light calibration operation may be performed. As described above, the external light calibration operation may be performed by removing the current component in the at least one light receiving unit 610a, which is generated while the at least one light emitting unit 610b emits no light.

In contrast, if the voltage signal output through the amplification circuit 650 falls outside the input dynamic range upon realtime monitoring, signals after falling outside the input dynamic range may not be measured and, thus, it is not known which biometric signal it is, causing performance deterioration upon biometric signal measurement. Thus, according to an embodiment, if the voltage signal output through the amplification circuit 650 upon realtime monitoring falls outside the input dynamic range, the external light calibration operation may be performed immediately regardless of whether the at least one light emitting unit 610b is in the off state.

To calibrate the external light in realtime, the wearable electronic device 301 may detect the external light component input together with the light component corresponding to the biometric signal and control to output only the biometric signal where the detected external light component has been removed.

To that end, the filter 665 of the external light calibration circuit 615 may be a filter for extracting the external light component. The filter 665 may perform filtering to extract the external light component every off period of the at least one light emitting unit 610b. The filter 665 may include at least one frequency band filter to filter at least one frequency band different from the actual biometric signal band to extract the external light. For example, for high-frequency band external light, only the external light component may be extracted using a high pass filter (HPF) having a band different from the biometric signal band. According to an embodiment, when the external light has a specific frequency pattern, the filter 665 may include a frequency band filter capable of extracting the specific frequency pattern.

The PID controller 670 may serve as a component to quickly estimate variations in the input signal, reflect it to the signal input to the at least one light receiving unit 610a to actively deal with signal variations due to the actual external light input.

The PID controller 670 may be an analog processor for removing the external light output from the filter 665 and generate a control value for the current pump 680 to make the magnitude of the external light zero. For example, the control signal from the PID controller 670 may be a voltage generated based on the output from the filter 665.

The inverter 675 may serve to operate the sink and source of the current pump 680 which is used to remove the DC component in the at least one light receiving unit 610a, e.g., photodiode, in a floating state. Here, the floating state may mean that the operation direction of the current pump 680 is not towards the ground GND. For example, the at least one light receiving unit 610a is connected to the amplification circuit (TIA) 650. Thus, to selectively adjust only the current of the at least one light receiving unit 610a, a current source and sink are needed. As two current pumps 680 are operated with the current direction changed by the inverter 675 to supply the same magnitude of current in different directions, the at least one light receiving unit 610a may become the floating state.

The current pumps 680 may include a first current pump operating as the source and a second current pump operating as the sink. The current pumps may be connected to the output terminal and input terminal, respectively, of the inverter 675, receive voltage signals from the output terminal and input terminal of the inverter 675, and output the current corresponding to the applied voltage signal to the input terminal of the at least one light receiving unit 610a. For example, when the input voltage of the inverter 675 is operated as the sink (or source), the output voltage of the inverter 675 may be connected with the input terminal of the current pump 680 to be the source (or sink).

The output terminal of the current pump 680 may be connected to the input terminal of the at least one light receiving unit 610a, so that the current pump 680 may input current to the at least one light receiving unit 610a, corresponding to the control signal, i.e., voltage signal, from the PID controller 670. As such, as the above-described operation is repeated, the signal output from the at least one light receiving unit 610a may be a signal where as much current component as the external light signal output from the at least one light receiving unit 610a has been removed, and only the biometric signal may pass through the amplification circuit 650 to the ADC 660, so that the biometric signal measurement may be obtained. According to an embodiment, use of such a feedback structure makes it possible to remove external light in realtime and thus measure only the reliable biometric signal.

The external light calibration circuit 615 may extract the external light signal using the filter 665 every off timing of the at least one light emitting unit 610b and perform the external light calibration operation (i.e., the operation of removing the external light signal/component from the biometric signal) through current input to the at least one light receiving unit 610a by the current pump 680, based on the external light signal extracted at the off timing of the at least one light emitting unit 610*b*, without extracting the external light signal every on timing of the at least one light emitting unit 610*b*. For example, the filter 665 or the current pump 680 may be configured to maintain the output at the off timing of the at least one light emitting unit 610*b*, even at the on timing of the at least one light emitting unit 610*b*.

According to certain embodiments, a wearable electronic device 301 may comprise a biometric signal detector (e.g., 310 of FIG. 3) including at least one light receiving unit 610*a* and at least one light emitting unit 610*b*, an external light calibration circuit 315, and a processor (e.g., 320 of FIG. 3) electrically connected with the biometric signal detector and the external light calibration circuit. The processor 320 may be configured to radiate light to a user's skin through the at least one light emitting unit 610*b*, detect an external light signal output through the at least one light receiving unit 610*a* during a second period among a first period during which the light is radiated through the at least one light emitting unit 610*b* and the second period during which the light is not radiated and remove the external light signal from a biometric signal corresponding to light reflected from the user's skin output through the at least one light receiving unit 610*a*, using the external light calibration circuit 315.

According to certain embodiments, the at least one light emitting unit 610*b* may include a light emitting diode (LED). The first period during which the light is radiated may be a period during which the LED is on, and the second period during which the light is not radiated may be a period during which the LED is off.

According to certain embodiments, the external light calibration circuit 315 may include a filter 665 configured to filter the external light signal, a proportional integral deviate (PID) controller 670 configured to generate a control signal for removing the external light signal output from the filter 665, an inverter 675 configured to apply a voltage signal corresponding to the control signal, and a current pump 680 configured to apply a current signal corresponding to the voltage signal from the inverter to the at least one light receiving unit 610*a*.

According to certain embodiments, the control signal for removing the external light signal may include a control signal for making a magnitude of the external light signal zero.

According to certain embodiments, the current pump 680 may include a first current pump 680*a* connected with an output terminal of the inverter 675 and a second current pump 680*b* connected to an input terminal of the inverter 675.

According to certain embodiments, the external light calibration circuit 315 may be configured to detect the external light signal by sampling every second period during which the light is not radiated.

According to certain embodiments, the external light calibration circuit 315 may remove the external light signal every first period during which the light is radiated.

According to certain embodiments, the wearable electronic device 301 may further comprise an amplification circuit 650 configured to convert a current signal output from the at least one light receiving unit 610*a* into a voltage signal and an analog-to-digital converter (ADC) 660 configured to convert the voltage signal into a digital signal.

According to certain embodiments, an output terminal of the amplification circuit 650 may be selectively connected with an input terminal of the external light calibration circuit 315 or an input terminal of the ADC 660 based on a first period during which the light is radiated and a second period during which the light is not radiated.

According to certain embodiments, a voltage signal output from the amplification circuit 650 during the second period during which the light is not radiated may be input to the filter 665.

According to certain embodiments, as a current by the current pump 680 is applied to the at least one light receiving unit 610*a*, a voltage signal output from the amplification circuit 650 during the first period during which the light is radiated may be input to the ADC 660.

According to certain embodiments, the voltage signal output from the amplification circuit 650 during the first period during which the light is radiated may include a signal where the external light signal is removed.

Figure 7:
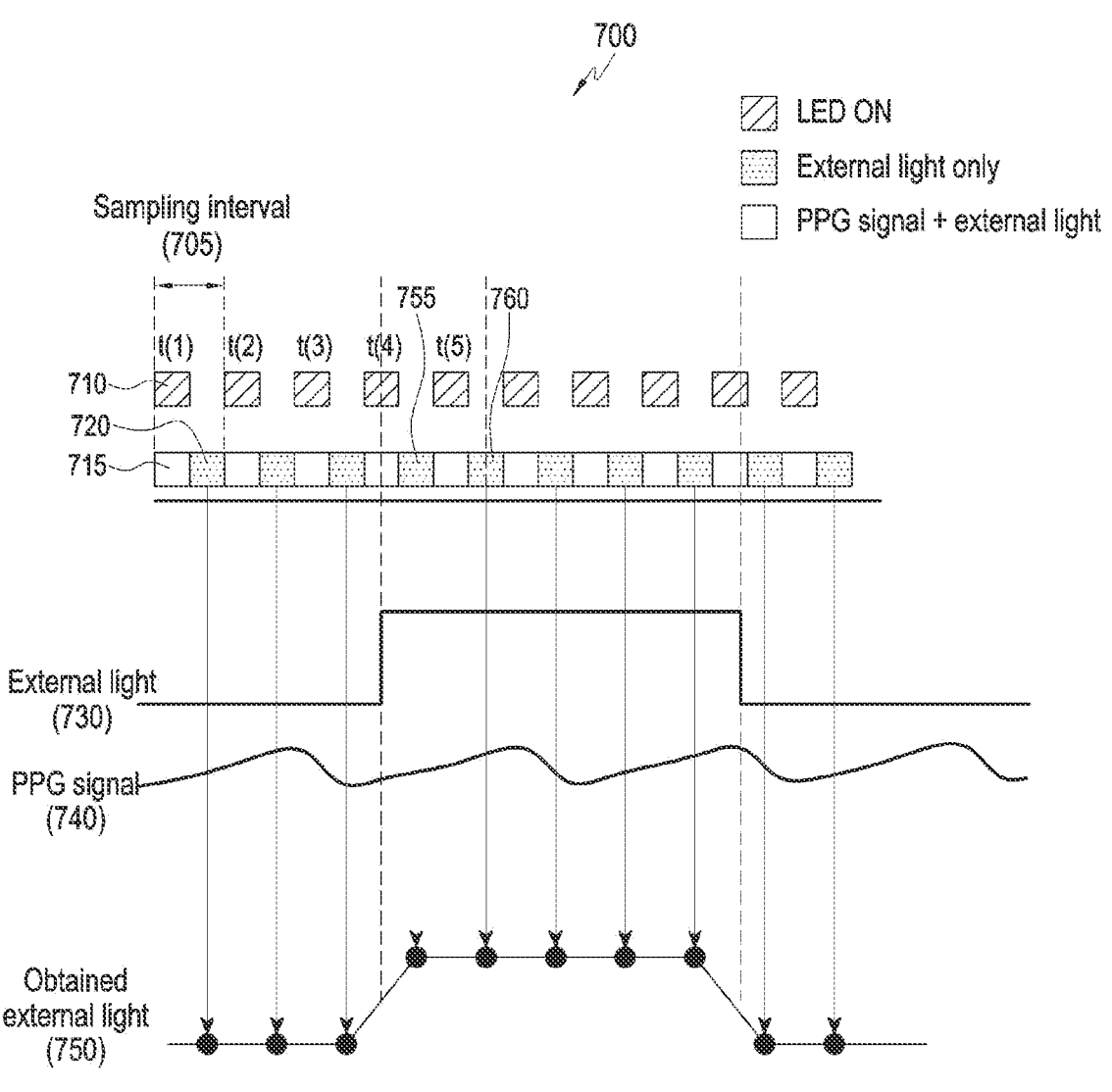
FIG. 7 is a view illustrating a method for selectively extracting external light in a filter of an external light calibration circuit according to certain embodiments.

FIG. 7 describes the operation of the electronic device when the external light 730 changes. The light emitting unit repeats between a first period 715 for radiating light, and second period 720 for not radiating light. A sampling interval 705 includes a first period 715 and a second period 720.

After each period when the light is radiates, t(1) . . . t(n), the light is not radiated. When light is not radiated, light detected by the light receiving unit is used to remove a portion of the light that is detected during the subsequent period when light is emitted. That is, the light received by the light receiving unit after t(k) is used to remove light from the light that is detected during t(k+1). When the external light 730 changes during t(4), during 755, the light receiving unit detects the changed external light. At t(5), the changed external light measured during 755 is used to remove external light. As a result, calibration occurs in real time, resulting in minimal data loss.

FIG. 7 is a view 700 illustrating a method for selectively extracting external light in a filter of an external light calibration circuit according to certain embodiments.

Referring to FIG. 7, when a sampling interval 705 includes the on time of the LED and the off time of the LED, the wearable electronic device 301 (e.g., the processor 320) may control the on/off operation of the LED to perform the operation of extracting and removing the external light in each sampling interval unit. As shown in FIG. 7, when the first LED on 710 time is t(1), the PPG signal and the external light signal 715 together enter the filter 665 during the t(1) 710 time, and the signal entering the filter 665 during the LED off time between t(1) and t(2) may be a signal 720 corresponding to external light. In other words, during the LED off time, only signals corresponding to the external light may be introduced. In this case, the signal entering the filter 665 may be a voltage signal converted into through the amplification circuit 650. Accordingly, the processor 320 may selectively extract and obtain only the signal corresponding to the external light when signals are sampled every LED off time. Accordingly, the PID controller 670 may know the magnitude (or intensity) of the external light output from the filter 665, so that although the PPG signal and the external light signal together are introduced, the magnitude of external light may be removed to leave only the PPG signal.

For example, when external light 730 with a high magnitude is introduced at t(4), the processor 320 may, at t(5), perform the calibration operation by subtracting the magnitude of the signal 755 corresponding to the external light between t(4) and t(5) from the signal at t(4). Further, the processor 320 may continuously perform the calibration operation every LED on timing, removing applied external light. For example, although a high magnitude of external light 730 is introduced after t(4), the processor 320 may continuously perform calibration as much as the external light 750 obtained in realtime every LED on timing, thus obtaining only the PPG signal 740 which is constantly introduced, without influence by noise, e.g., external light, and thus allowing for stable biometric measurement.

Figure 8:
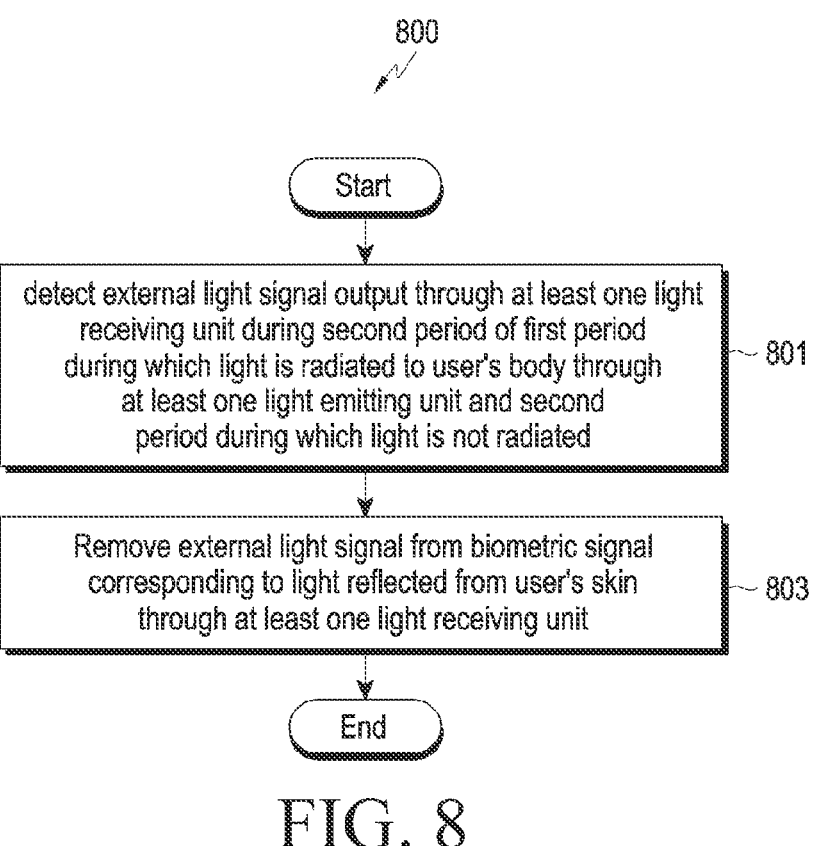
FIG. 8 is a flowchart illustrating an operation for performing an external light calibration method in a wearable electronic device according to certain embodiments.

FIG. 8 is a flowchart 800 illustrating an operation for performing an external light calibration method in a wearable electronic device according to certain embodiments. Referring to FIG. 8, the operation method may include operations 801 to 803. Each step/operation of the operation method of FIG. 8 may be performed by at least one of a wearable electronic device (e.g., the electronic device 101 of FIG. 1 or the biometric signal processing device 301 of FIG. 3) or at least one processor (e.g., the processor 120 of FIG. 1 or the processor 320 of FIG. 3) of the wearable electronic device.

The wearable electronic device 301 (e.g., the processor 320) may start measuring a biometric signal. According to an embodiment, when a wearing of the wearable electronic device on the user's body is detected, a signal of the detection may be determined to be an 'input or request for measurement.' For example, when the wearable electronic device is attached to the user's body, if the signal input through at least one sensor included in the wearable electronic device is first received, the wearable electronic device may determine that the first signal is an 'input or request for measurement.' According to an embodiment, when its wearing is detected, the wearable electronic device 301 may switch to an operation mode for biometric signal measurement and start measurement. According to an embodiment, measurement of the biometric signal in the wearable electronic device 301 may be allowed to start and end by the user's manipulation on the wearable electronic device 301 or an electronic device (e.g., smartphone) interworking with the wearable electronic device 301. According to an embodiment, measurement may be allowed to start using the on/off function.

As described above, if biometric signal measurement starts, light may be radiated to the user's skin through at least one light emitting unit. Accordingly, in operation 801, the wearable electronic device 301 may detect the external light signal output through at least one light receiving unit during a second period among a first period during which light is radiated to the user's body through the at least one light emitting unit and the second period during which the light is not radiated. The first period during which the light is radiated may be a period during which the light emitting unit is on, and the second period during which the light is not radiated may be a period during which the light emitting unit is off.

In operation 803, the wearable electronic device 301 may remove the external light signal from the biometric signal corresponding to the light reflected from the user's skin, output through the at least one light receiving unit.

According to certain embodiments, the external light calibration method may include filtering the external light signal, generating a control signal for removing the external light signal output through the filtering, applying a voltage signal corresponding to the control signal, and applying a current signal corresponding to the voltage signal to the at least one light receiving unit.

According to certain embodiments, detecting the external light signal may include detecting the external light signal by sampling every second period during which the light is not radiated.

According to certain embodiments, removing the external light signal may include removing the external light signal every first period during which the light is radiated.

According to certain embodiments, the external light calibration method may further include converting the current signal output from the at least one light receiving unit into a voltage signal and converting the voltage signal into a digital signal.

According to certain embodiments, as a current signal corresponding to the voltage signal is applied to the at least one light receiving unit, a current signal output from the at least one light receiving unit during a first period during which the light is radiated may include a signal where the external light signal is removed.

Figure 9:
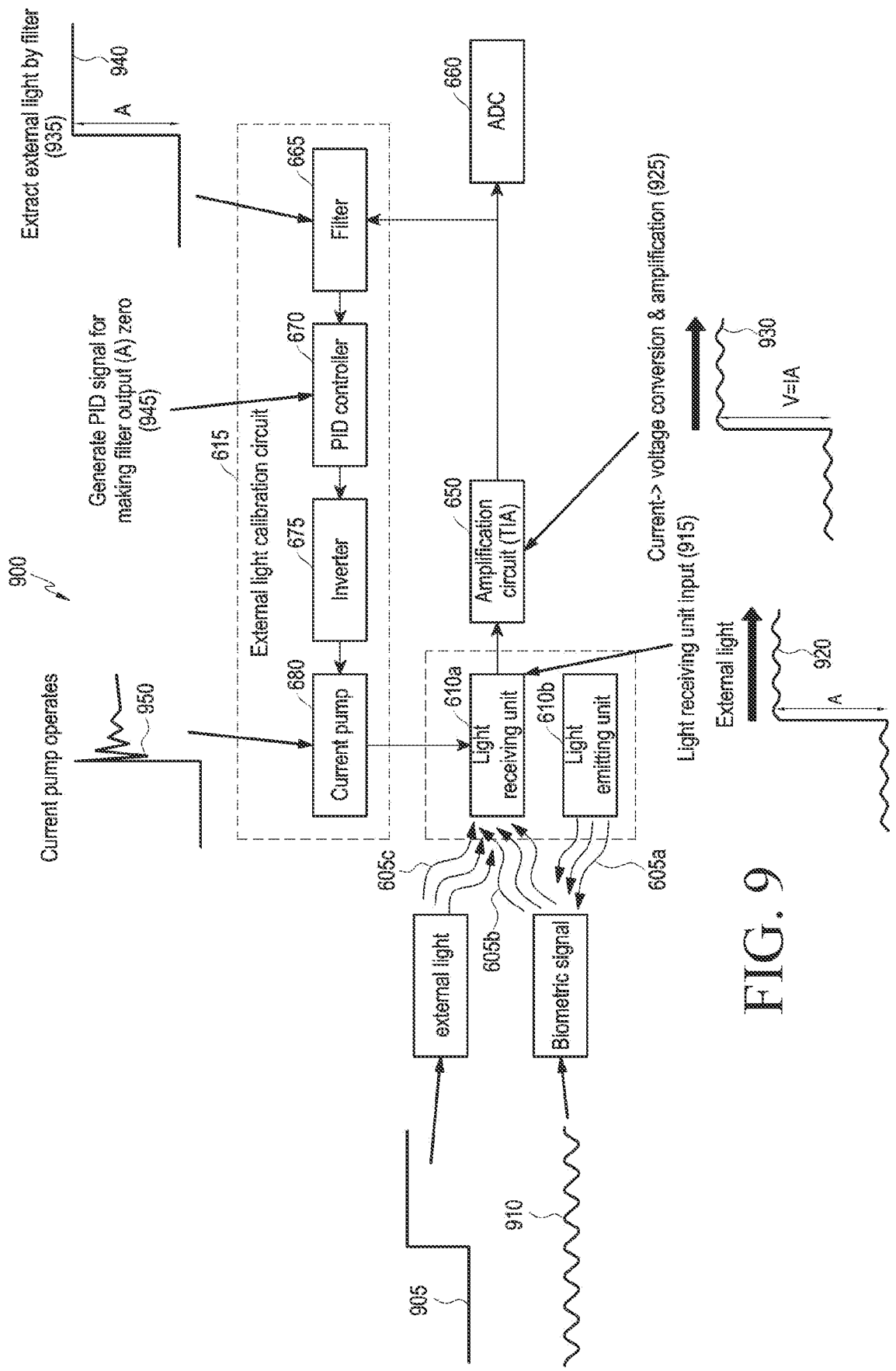
FIG. 9 is a view illustrating a signal upon initial external light calibration according to certain embodiments.

FIG. 9 is a view 900 illustrating a signal upon initial external light calibration according to certain embodiments.

The wearable electronic device 301 (e.g., the processor 320) may receive a biometric signal 910 using at least one light emitting unit 610*b* and at least one light receiving unit 610*a*.

Referring to FIG. 9, the reflected light 605*b* by the light 605*a* radiated in the on state of the at least one light emitting unit 610*b* may be received through the at least one light receiving unit 610*a* and, at this time, external light 605*c* may be received together. For example, when the biometric signal 910 of the reflected light 605*b* by the light 605*a* radiated to the user's body, along with the external light signal 905, is introduced to the at least one light receiving unit 610*a*, a signal 920 with current magnitude A may be output through the at least one light receiving unit 610*a* upon input 915 to the light receiving unit. In other words, a signal whose current magnitude has suddenly been increased by A may be output. Accordingly, the amplification circuit 650 may output a voltage signal 930 with magnitude V from the current signal with magnitude A, through voltage conversion and amplification 925.

According to an embodiment, when a signal falling outside the input dynamic range is output from the amplification circuit 650 while the signal from the amplification circuit 650 is sampled in realtime every constant sampling interval, the processor 320 may perform the operation 935 of extracting the external light by the filter 665, extracting the voltage signal with magnitude A. Here, the voltage signal with magnitude A may be a voltage signal extracted at the LED off timing. Alternatively, the voltage signal with magnitude A may be a voltage signal extracted by the filter 665 for extracting only external light with a band different from that of the biometric signal.

In proportion to the voltage signal output from the filter 665, the PID controller 670 may generate (945) a PID signal for making the voltage signal zero. Accordingly, the current pump 680 may output the current signal 950 corresponding to the voltage signal by the PID controller 670 and be applied to the input terminal of the at least one light receiving unit 610*a*.

Here, the processor 320 may temporarily stop processing for obtaining the biometric signal on the signal output through the amplification circuit 650 while the external light calibration operation is performed as a voltage change is initially caused due to external light. Accordingly, the signal output through the amplification circuit 650 is not transferred to the ADC 660 not to be used as a biometric signal measurement and may be treated as loss. Since the blanking region where it is treated as loss corresponds to a very small region, it may have no influence on the biometric signal measurement.

The external light calibration operation is performed with the above-described feedback structure, which is described in detail with reference to FIG. 10.

Figure 10:
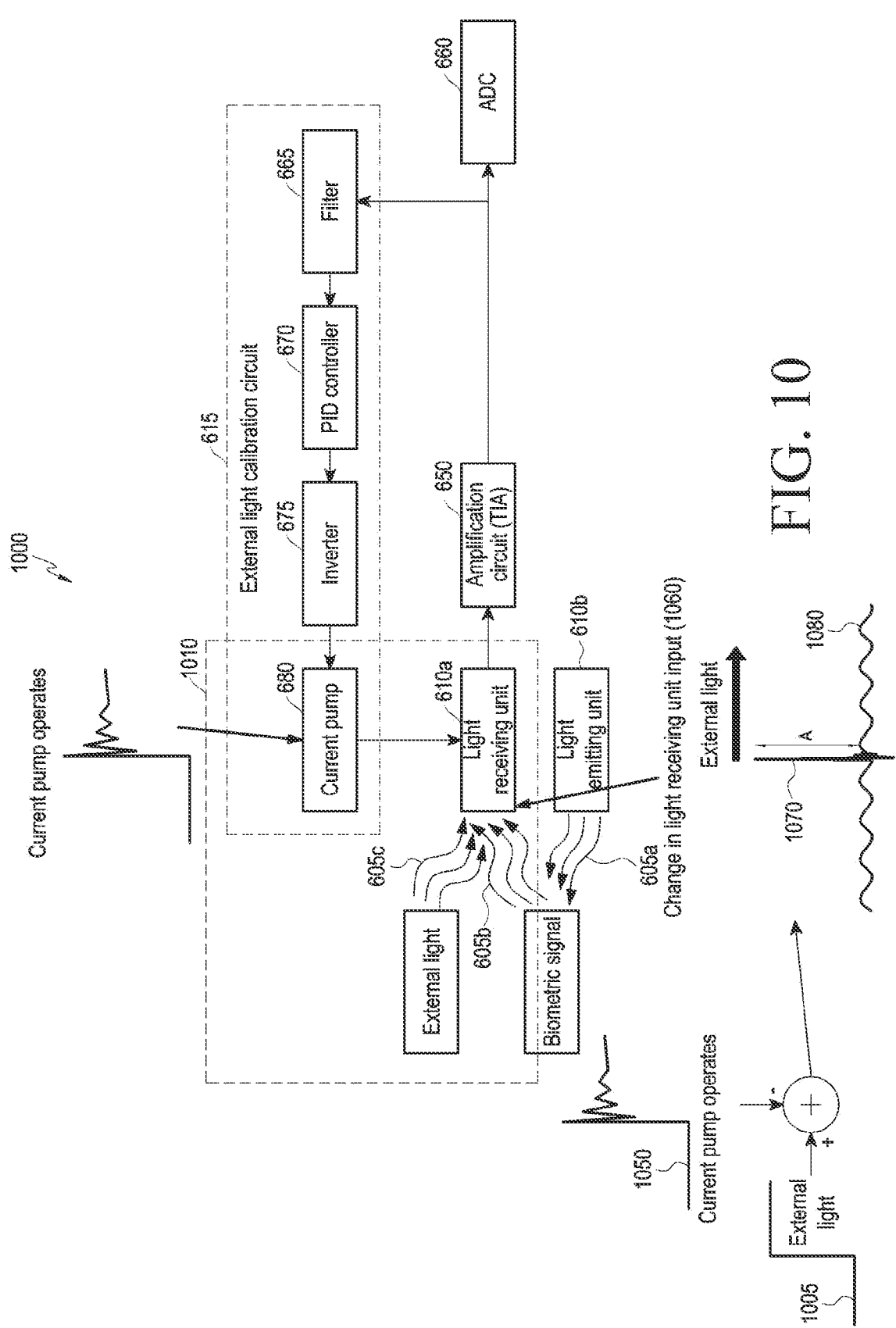
FIG. 10 is a view illustrating a signal after external light calibration according to certain embodiments.

FIG. 10 is a view 1000 illustrating a signal after external light calibration according to certain embodiments.

As shown in FIG. 10, when external light is first detected upon realtime biometric signal measurement, the wearable electronic device 301 (e.g., the processor 320) may remove the external light component through the external light calibration operation from the next sampling period so that no voltage change due to external light influence occurs over time. The operation 1010 of at least one light receiving unit 610a and the current pump 680 for removing the external light component is described below.

For example, although the signal of the reflected light 605b by the light 605a radiated to the user's body, together with the external light signal 1005, is introduced to the at least one light receiving unit 610a, the current signal 1050 from the current pump 680 is applied to the input terminal of the at least one light receiving unit 610a, so that a signal 1080 offset as much as the external light may be output. As such, in the case of an input change 1060 in the at least one light receiving unit 610a, a signal whose current magnitude is increased by, e.g., A, in response to sudden introduction of the external light temporarily appears and then only a signal corresponding to the biometric signal 1080 where it has been removed may be input to the amplification circuit 650.

As described above, the processor 320 may disregard some signal 1070 obtained in a certain initial period and, in such a case, although there is sudden external light input, it is possible to obtain only the biometric signal 1080 within the input dynamic range, rendering it possible to stably obtain the biometric signal.

Figure 11:
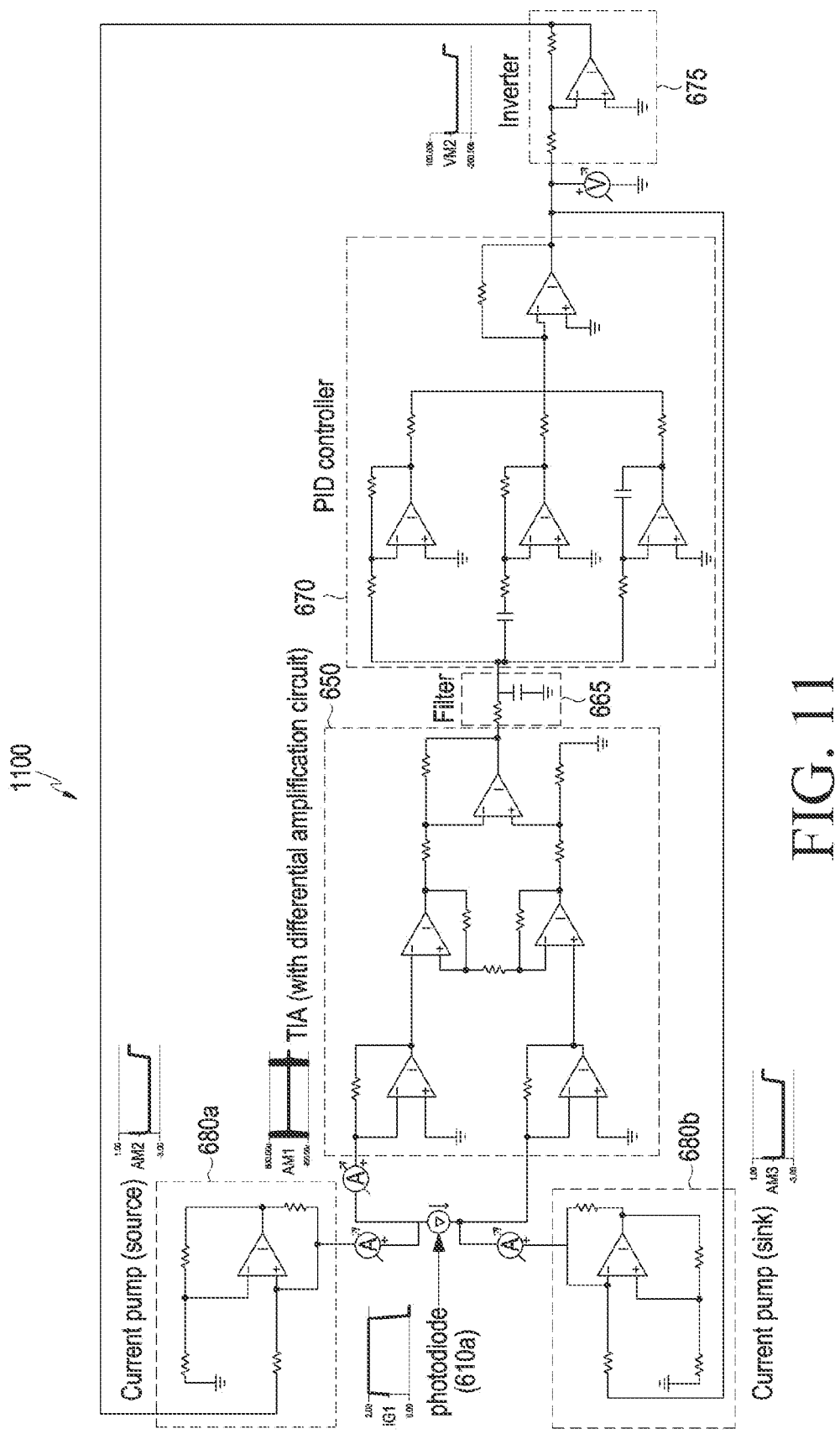
FIG. 11 is a detailed circuit diagram for external light calibration according to certain embodiments.

FIG. 11 is a detailed circuit diagram 1100 for external light calibration according to certain embodiments.

As shown in FIG. 11, the first current pump 680a operating as the source and the second current pump 680b operating as the sink may apply current to the photodiode 610a in response to the control signal of the PID controller 670. The amplification circuit 650 may include a differential amplification circuit and, when the output signal of the amplification circuit 650 includes the external light signal and the biometric signal both, filter only the external light signal using the filter 665. If only the external light signal is extracted using the filter 665, the PID controller 670 may output a control signal (or voltage signal) for making the input corresponding to the external light signal zero through the inverter 675.

Figure 12:
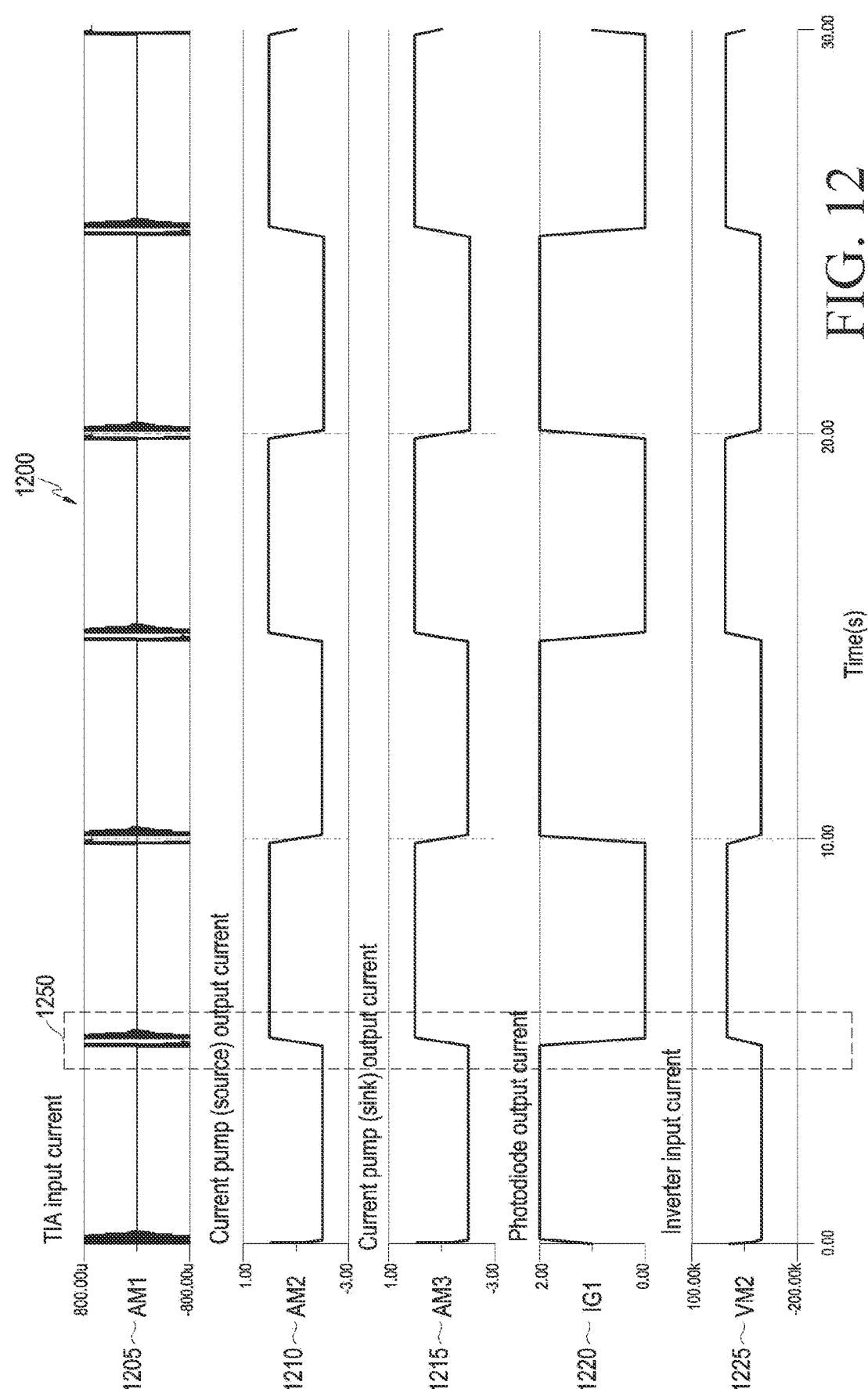
FIG. 12 is a view illustrating an output of each component after external light calibration according to certain embodiments.

FIG. 12 is a view 1200 illustrating comparison the respective outputs of the components (e.g., the current pumps 680a and 680b, the photodiode 610a, and the inverter 675) after external light calibration according to certain embodiments.

As shown in FIG. 12, when the current generated from the photodiode 610a is IG1 1220, if AM2 1210 and AM3 1215 which are output currents of the current pumps 680a and 680b for removing the current generated from the photodiode 610a in response to VM2 1225 which is the input current of the inverter 675 are applied, it may be seen that, for AM1 1205 indicating the current input to TIA which is the amplification circuit 650, a mere temporary blanking region occurs every sampling period, and AM1 1205 with a constant magnitude is output.

As shown in FIG. 12, despite a sudden DC variation in IG1 1220, e.g., although it is varied with a large width, such as 0→2→0 . . . , AM1 1205 corresponding to the calibrated result may be output with a constant magnitude as the DC component is calibrated. In this case, it may be seen that a signal, i.e., AM2 1210, which is opposite to IG1 1220 which is the current generated from the photodiode 610a is applied to the external light calibration circuit 615 for calibration. As described above, it may be identified that for an abrupt external light condition, e.g., a step input of IG1 1220, the calibration circuit (AM2 1210 or AM3 1215) is quickly operated to output AM1 1205 and is thus not influenced by the DC value of IG1 1220.

Here, it may be seen that temporary noise 1250 is caused in AM1 1205 which is the result of calibration for sudden application of the external light, and this may be noise generated when the PID controller 670 is operated. The noise region may be referred to as a blanking region, which is described in detail with reference to FIG. 13.

Figure 13:
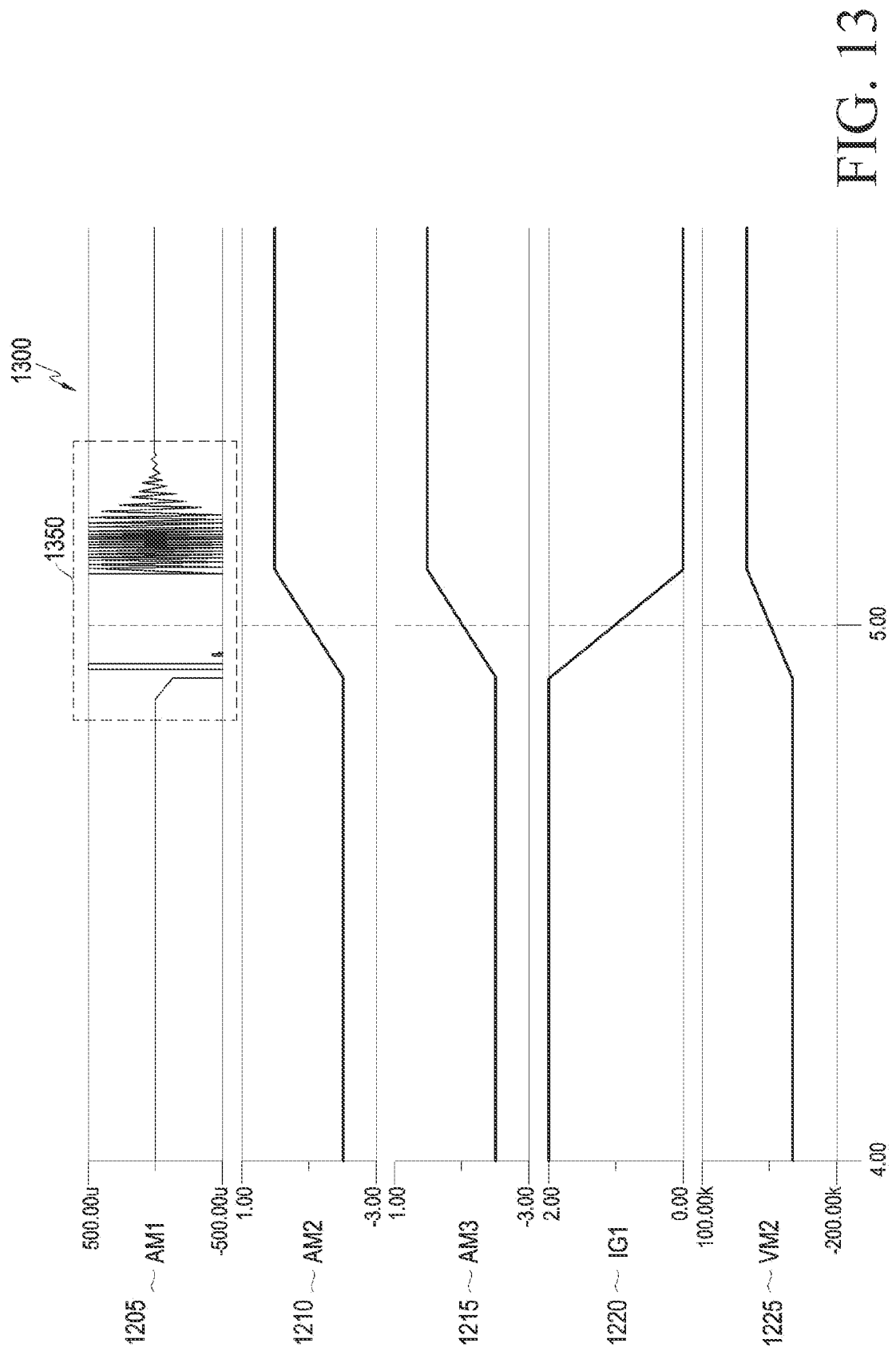
FIG. 13 is a view illustrating comparison between the respective outputs of components upon initial external light calibration according to certain embodiments.

FIG. 13 is a view 1300 illustrating comparison between the respective outputs of components upon initial external light calibration according to certain embodiments. In particular, FIG. 13 is an example enlarged view of the region 1250 instantaneously caused by the PID controller 670 at the time of application of the external light of FIG. 12.

As shown in FIG. 13, it may be seen that if the region 1250 of FIG. 12 is enlarged, an oscillation 1350 is generated. The generation period and magnitude of the oscillation 1350 may be finely tuned by changing the value of the element constituting the PID controller 670. FIG. 13 shows an example of one option to allow the PID controller 670 to operate as over damping to quickly adjust to the baseline. The value of the element constituting the PID controller 670 may be modified to further shorten the region of oscillation 1350, and data loss may be minimized by decreasing the region of the oscillation 1350. As described above, according to certain embodiments, it is possible to quickly remove noise through analog signal processing through realtime feedback structure. Thus, internal computation for discretely adjusting the DC current is not required, and it is needless to adjust the intensity of the internal light source to reduce influence of external light. Thus, SNR may be maintained.

According to certain embodiments, a wearable electronic device, comprises: at least one light receiving unit; at least one light emitting unit; an external light calibration circuit; and a processor electrically connected with the at least one light receiving unit, at least one light emitting unit, and the external light calibration circuit, wherein the processor is configured to: control the at least one light emitting unit to radiate light during first periods, and not emit light during second periods, and detect light through the at least one light receiving unit during the second periods, and controlling the external light calibration circuit to provide an input to the at least one light receiving unit during first periods, based on the light detected during the second periods; and wherein during the first periods the at least one light receiving unit provides an output based on light received, and the input from the external light calibration circuit.

According to certain embodiments, the at least one light emitting unit includes a light emitting diode (LED), and during the first periods the LED is on, and during the second periods the LED is off.

According the certain embodiments, the external light calibration circuit includes: a filter configured to filter a light signal corresponding to detected light, thereby resulting in a filtered light signal; a proportional integral deviate (PID) controller configured to generate a control signal for removing the filtered light signal output from the filter; an inverter configured to apply a voltage signal corresponding to the control signal; and a current pump configured to apply a current signal corresponding to the voltage signal from the inverter to the at least one light receiving unit.

According to certain embodiments, the control signal for removing the filtered light signal includes a control signal for making a magnitude of the filtered light signal zero.

According to certain embodiments, the current pump includes a first current pump connected with an output terminal of the inverter and a second current pump connected to an input terminal of the inverter.

According to certain embodiments, the external light calibration circuit is configured receive the light signal by sampling every second period.

According to certain embodiments, the wearable electronic device further comprises: an amplification circuit configured to convert a current signal output from the at least one light receiving unit into a voltage signal; and an analog-to-digital converter (ADC) configured to convert the voltage signal into a digital signal.

According to certain embodiments, an output terminal of the amplification circuit is selectively connected with an input terminal of the external light calibration circuit or an input terminal of the ADC based on the first periods or second periods, and wherein a voltage signal output from the amplification circuit during the second periods is not radiated is input to the filter.

According to certain embodiments, a current by the current pump is applied to the at least one light receiving unit, a voltage signal output from the amplification circuit during the first periods is input to the ADC, and wherein the voltage signal output from the amplification circuit during the first periods includes a signal where a portion of the signal corresponding to external light is removed.

According to certain embodiments, the at least one light receiving unit comprises a photodiode.

According to certain embodiments, a method for calibrating external light for biometric signal measurement in a wearable electronic device, comprises: radiating light with at least one light emitting unit during first periods and not radiating light during second periods; detecting a light signal output by at least one light receiving unit during the second periods; and providing an input to the at least one light receiving unit during the first periods by an external light calibration circuit, wherein the input is based on the detected light signal; provides an output during the first periods based on light received and the input by the at least one light emitting unit.

According to certain embodiments, the at least one light emitting unit includes a light emitting diode (LED), and wherein during the first periods the LED is on, and during the second periods the LED is off.

According to certain embodiments, providing the input comprises: filtering the light signal, thereby resulting in a filtered light signal; generating a control signal for removing the filtered light signal; applying a voltage signal corresponding to the control signal with an inverter; and applying a current signal corresponding to the voltage signal to the at least one light receiving unit with a current pump.

According to certain embodiments, the control signal for removing the filtered light signal includes a control signal for making a magnitude of the filtered light signal zero.

According to certain embodiments, the current pump includes a first current pump connected with an output terminal of the inverter and a second current pump connected to an input terminal of the inverter.

According to certain embodiments, detecting the light signal includes detecting the light signal by sampling every second period.

According to certain embodiments, the method further comprises converting a current signal output from the at least one light receiving unit into a voltage signal with an amplifier; and converting the voltage signal into a digital signal with an analog-to-digital converter (ADC).

According to certain embodiments, the method further comprises: connecting an output terminal of the amplifier to an input terminal of the ADC during first periods; and connecting the output terminal of the amplifier to an input terminal of the external light calibration circuit during second periods.

According to certain embodiments, as a current signal corresponding to the voltage signal is applied to the at least one light receiving unit, a current signal output from the at least one light receiving unit during a first period includes a signal where a portion of the signal corresponding to external light signal is removed.

According to certain embodiments, the at least one light receiving unit comprises a photodiode.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, The module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. Some of the plurality of entities may be separately disposed in different components. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

There may be provided a storage medium storing instructions configured to, when executed by at least one processor, enable the at least one processor to perform at least one operation which may comprise radiating light to a user's skin through at least one light emitting unit, detecting an external light signal output through at least one light receiving unit during a second period among a first period during which the light is radiated through the at least one light emitting unit and the second period during which the light is not radiated, and removing the external light signal from a biometric signal corresponding to light reflected from the user's skin output through the at least one light receiving unit.

The embodiments herein are provided merely for better understanding of the present invention, and the present invention should not be limited thereto or thereby. It should be appreciated by one of ordinary skill in the art that various changes in form or detail may be made to the embodiments without departing from the scope of the present invention defined by the following claims.

What is claimed is:

1. A wearable electronic device, comprising:
at least one light receiving unit;
at least one light emitting unit;
an external light calibration circuit; and
a processor electrically connected with the at least one light receiving unit, at least one light emitting unit, and the external light calibration circuit,
wherein the processor is configured to:
control the at least one light emitting unit to radiate light during first periods, and not emit light during second periods,
respectively detect a first light during the first periods and a second light during the second periods through the at least one light receiving unit, and
remove, by the external light calibration circuit, a second light signal, which corresponds to the second light detected during the second periods, from a first light signal, which corresponds to the first light and includes biometric information during the first periods,
wherein the external light calibration circuit is configured to receive the second light signal every second period and remove the second light signal from the first light signal every first period, and
wherein the external light calibration circuit includes:
a filter configured to filter the second light signal corresponding to detected second light, thereby resulting in a filtered light signal;
a proportional integral deviate (PID) controller configured to generate a control signal for removing the filtered light signal output from the filter;
an inverter configured to apply a voltage signal corresponding to the control signal; and
a current pump configured to apply a current signal corresponding to the voltage signal from the inverter to the at least one light receiving unit.

2. The wearable electronic device of claim 1, wherein the at least one light emitting unit includes a light emitting diode (LED), and
wherein during the first periods the LED is on, and during the second periods the LED is off.

3. The wearable electronic device of claim 1, wherein the control signal for removing the filtered light signal includes a control signal for making a magnitude of the filtered light signal zero.

4. The wearable electronic device of claim 1, wherein the current pump includes a first current pump connected with an output terminal of the inverter and a second current pump connected to an input terminal of the inverter.

5. The wearable electronic device of claim 1, further comprising:
an amplification circuit configured to convert a current signal output from the at least one light receiving unit into a voltage signal; and
an analog-to-digital converter (ADC) configured to convert the voltage signal into a digital signal.

6. The wearable electronic device of claim 5, wherein an output terminal of the amplification circuit is selectively connected with an input terminal of the external light calibration circuit or an input terminal of the ADC based on the first periods or second periods, and

33 wherein a voltage signal output from the amplification circuit during the second periods is not radiated is input to the filter.

7. The wearable electronic device of claim 6, wherein as a current by the current pump is applied to the at least one light receiving unit, a voltage signal output from the amplification circuit during the first periods is input to the ADC, and wherein the voltage signal output from the amplification circuit during the first periods includes a signal where a portion of the signal corresponding to external light is removed.

8. The wearable electronic device of claim 1, wherein the at least one light receiving unit comprises a photodiode.

9. A method for calibrating external light for biometric signal measurement in a wearable electronic device, the method comprising:

radiating light with at least one light emitting unit during first periods and not radiating light during second periods;

respectively detecting a first light signal during the first periods and a second light during the second periods through at least one light receiving unit; and removing, by the external light calibration circuit, a second light signal, which corresponds to the second light detected during the second periods, from a first light signal, which corresponds to the first light and includes biometric information during the first periods, wherein the external light calibration circuit is configured to receive the second light signal every second period and remove the second light signal from the first light signal every first period, and wherein providing the input comprises:

filtering the second light signal, thereby resulting in a filtered light signal;

generating a control signal for removing the filtered light signal;

applying a voltage signal corresponding to the control signal with an inverter; and applying a current signal corresponding to the voltage signal to the at least one light receiving unit with a current pump.

10. The method of claim 9, wherein the at least one light emitting unit includes a light emitting diode (LED), and wherein during the first periods the LED is on, and during the second periods the LED is off.

11. The method of claim 9, wherein the control signal for removing the filtered light signal includes a control signal for making a magnitude of the filtered light signal zero.

12. The method of claim 9, wherein the current pump includes a first current pump connected with an output terminal of the inverter and a second current pump connected to an input terminal of the inverter.

13. The method of claim 9, further comprising:

converting a current signal output from the at least one light receiving unit into a voltage signal with an amplifier; and converting the voltage signal into a digital signal with an analog-to-digital converter (ADC).

14. The method of claim 13, further comprising:

connecting an output terminal of the amplifier to an input terminal of the ADC during first periods; and connecting the output terminal of the amplifier to an input terminal of the external light calibration circuit during second periods.

15. The method of claim 14, wherein as a current signal corresponding to the voltage signal is applied to the at least one light receiving unit, a current signal output from the at least one light receiving unit during a first period includes a signal where a portion of the signal corresponding to external light signal is removed.

16. The method of claim 9, wherein the at least one light receiving unit comprises a photodiode.

17. The wearable electronic device of claim 1, wherein an output terminal of the external light calibration circuit is directly connected to an input terminal of the at least one light receiving unit.

18. The wearable electronic device of claim 1, wherein an output terminal of the external light calibration circuit applies current corresponding to the second light signal to the input terminal of the at least one light receiving unit.

* * * * *